United States Patent [19]

Kirchhoff

[11] Patent Number: 4,638,078

[45] Date of Patent: Jan. 20, 1987

[54] ARYLCYCLOBUTENYL AMIDO ALKENOIC ACIDS AND SALTS THEREOF

[75] Inventor: Robert A. Kirchhoff, Midland, Mich.

[73] Assignee: The Dow Chemical Company, Midland, Mich.

[21] Appl. No.: 727,162

[22] Filed: Apr. 25, 1985

[51] Int. Cl.$^4$ .................. C07C 121/64; C07C 103/34
[52] U.S. Cl. .................. 558/414; 260/501.1; 548/546; 548/547; 548/548; 548/549; 558/426; 560/10; 560/21; 560/37; 560/42; 560/45; 560/48; 562/427; 562/435; 562/450; 562/455; 562/457
[58] Field of Search .................. 260/465 D, 501.1; 548/546, 549; 562/450, 457, 427, 435, 455; 558/414, 426; 560/10, 21, 37, 42, 45, 48

[56] References Cited

U.S. PATENT DOCUMENTS

| | | | |
|---|---|---|---|
| 3,053,851 | 9/1962 | Ladd | 548/549 |
| 3,265,708 | 8/1966 | Stiteler | 260/326.5 |
| 3,334,071 | 8/1967 | Reeder | 260/78 |
| 3,352,832 | 11/1967 | Barr et al. | 260/78 |
| 3,426,228 | 2/1969 | Barrie et al. | 310/215 |
| 4,132,715 | 1/1979 | Roth | 260/326.26 |
| 4,376,206 | 3/1983 | Oba et al. | 548/546 |

OTHER PUBLICATIONS

Zhubanov et al., Chemical Abstracts, vol. 82, 112305c (1975).
Shur et al., Chemical Abstracts, vol. 69, 97409a (1968).
Fortschr. Hochpolym-Forsch, Bd. 3 *Diels-Alder Polymerization*, pp. 48-58 (19061).

*Primary Examiner*—Dolph H. Torrence
*Attorney, Agent, or Firm*—Norman L. Sims

[57] ABSTRACT

The invention is a compound which comprises an amido alkenoic acid or a water-soluble salt thereof and and arylcyclobutene moiety, wherein the cyclobutene moiety is fused to the aryl radical, and wherein the amide nitrogen is connected to the aryl radical of the arylcyclobutenyl moiety by a direct bond or a bridging member.

19 Claims, No Drawings

ARYLCYCLOBUTENYL AMIDO ALKENOIC ACIDS AND SALTS THEREOF

BACKGROUND OF THE INVENTION

This invention relates to arylcyclobutenyl amido alkenoic acids and salts thereof.

In recent years the search for high performance materials, especially high temperature-resistant polymers, has gained momentum. In order for a material to have stability at high temperatures, it must fulfill several requirements including a high melting or softening temperature, a high modulus or rigidity, a resistance to solvent and chemical degradation, and toughness. The intrinsic thermal and oxidative stability of aromatic structures has long been recognized, and a variety of polymers have been made in which benzene rings are linked together by various connecting groups. Among the more stable aromatic polymers that fulfill the requirements of high temperature resistance are the polybenzimidazoles, the polybenzoxazoles and the polyimides. Of these polymers, the polyimides have had the most interest.

The major difficulty encountered in the commercial development of these materials is that they are usually obtained in the form of a powder which cannot be readily fabricated into useful objects.

The polyimides prepared from aliphatic diamines and aromatic carboxylic acids are generally soluble and thermoplastic. Aliphatic polyimides have been prepared from bis(dienophiles) and a bis diene. Such reactions often involve gas evolution.

Aromatic polyimides, such as polypyromellitimides, have a spectrum of superior properties. These polyimides may be prepared by the reaction of an aromatic dianhydride with an aromatic diamine to give a soluble polyamic acid, which on cyclodehydration gives the insoluble desired product.

High performance plastics reduce the weight of mechanical components, and not just by virtue of their densities. Their high performance properties allow greater design stresses, and often elements can be downsized accordingly. In recent years, aromtic polyimides have become widely accepted as premium, high performance engineering plastics. These resins are well-known for having excellent properties at elevated temperatures (i.e., chemical resistance) but are also costly. Historically, polyimide resins are difficult to fabricate into objects other than fibers and films. The most common methods of manufacturing parts having the highest strength and temperature properties are hot compression-molding, machining from hot-compression molded or extruded rod, and direct forming (a process similar to the powder-metallurgy processes). Given the synthetic and fabrication difficulties, a new route to polyimides is desirable.

A further problem with the preparation of certain polyimides is the need for the use of catalysts, initiators or curing agents. The presence of such compounds often results in the preparation of impure polymeric compositions. Further, the presence of such compounds often results in undesirable properties in such polymeric compositions. Many of the monomers used to prepare polyimides are water-insoluble. What is needed are monomers which prepare polyimides wherein the polymers can be easily processed, for example, fabricated into useful objects. What is further needed are monomers which can be polymerized in a manner such that no volatile gas is evolved. What is further needed are monomers which can be polymerized without the need for catalysts, curing agents or initiators. Monomers which are water-soluble are needed.

SUMMARY OF THE INVENTION

The invention is a compound which comprises an amido alkenoic acid or a water-soluble salt thereof and an arylcyclobutene moiety, wherein the cyclobutene moiety is fused to the aryl radical, and wherein the amide nitrogen is connected to the aryl radical of the arylcyclobutenyl moiety by a bridging member or a direct bond.

The novel compounds of this invention are useful in preparing thermoset polymers. These compounds are also intermediates in the preparation of N-substituted arylcyclobutenyl unsaturated cyclic imides. The cyclic imides are useful in preparing thermoset polymers.

The salts of the arylcyclobutenyl amido alkenoic acids of this invention are water-soluble. These compounds can be polymerized from aqueous solution. Alternatively, the monomers can be deposited on a substrate surface using an aqueous solution of such compounds. The N-substituted arylcyclobutenyl unsaturated imides prepared from the novel compounds of this invention are water-insoluble. The polymers prepared from both classes of compounds are similar in structure and properties.

The novel compounds of this invention are easily processable into useful articles. Furthermore, in order to prepare the polymers of these monomers, there is no need for catalysts, initiators or curing agents.

DETAILED DESCRIPTION OF THE INVENTION

In general, the compounds of this invention comprise amido alkenoic acids or water-soluble salts thereof which are N-substituted with arylcyclobutene moieties. In such arylcyclobutene moieties the cyclobutene ring is fused to the aromatic radical. The nitrogen atom of the amide is connected to the aryl radical of the arylcyclobutene moiety by a bridging member or a direct bond. The amido alkenoic acid or water-soluble salt thereof can be substituted with hydrocarbyl, hydrocarbyloxy or hydrocarbylthio substituents. The aryl radical on the arylcyclobutene moiety can be substituted with electron-withdrawing groups, electron-donating groups, hydrocarbyl groups, hydrocarbyloxy groups or hydrocarbylthio groups. The cyclobutene ring may be substituted with electron-withdrawing groups.

The amido alkenoic acid can be any alkene which is substituted with amide and carboxylic acid moieties, or a water-soluble salt of the carboxylic acid. In one preferred embodiment the amido alkenoic acid is capable of cyclization when exposed to dehydration conditions, and may be substituted as described hereinbefore.

Water-soluble salt of the amido alkenoic acid refers herein to the compounds of this invention in which the carboxyl moiety of the alkenoic acid is converted to a water-soluble salt by replacing the hydrogen atom with the cation from a base. Preferred bases from which the cation is derived include alkali metal bases, alkaline earth metal bases, ammonia, primary or secondary amines and the like. More preferred bases include ammonia, and primary or secondary amines. Ammonia is the most preferred base.

It is preferable that the olefinic unsaturation be adjacent to either the acid or amide carbonyl moiety. In one more preferred embodiment, the amido alkenoic acid has 2 carbon atoms between the amide and carboxylic acid carbon atoms. In particular, it is an amido butenoic acid. Preferably, the substituents which may be on the carbon atoms of the alkenoic chain are $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ alkaryl, $C_{7-20}$ alkaryloxy, $C_{7-20}$ alkarylthio, $C_{7-20}$ aralkyl, $C_{7-20}$ aralkoxy or $C_{7-20}$ aralkylthio. More preferred substituents include $C_{1-20}$ alkyl, with $C_{1-3}$ alkyl being most preferred.

The arylcyclobutene moiety can be any aromatic radical which has a cyclobutene ring fused to one of the aromatic rings. The term "aryl" refers herein to any aromatic radical. Preferred aromatic radicals include benzene, naphthalene, phenanthrene, anthracene, a biaryl radical, or two or more aromatic radicals bridged by alkylene or cycloalkylene moieties. More preferred aromatic radicals include benzene, naphthalene, biphenyl, binaphthyl or a diphenylalkylene or a diphenylcycloalkylene compound. The most preferred aromatic radical is benzene.

The aryl radical can be substituted with electron-withdrawing groups, electron-donating groups, hydrocarbyloxy groups, hydrocarbyl groups or hydrocarbylthio groups. Electron-withdrawing groups refer herein to cyano, carboxylate, hydrocarbylcarbonyloxy, nitro, halo, hydrocarbylsulfinyl or hydrocarbylsulfonyl groups. Electron-donating groups refer herein to amino groups. Preferred substituents on the aryl radical include $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ alkaryl, $C_{7-20}$ alkaryloxy, $C_{7-20}$ alkarylthio, $C_{7-20}$ aralkyl, $C_{7-20}$ aralkoxy, $C_{7-20}$ aralkylthio, cyano, carboxylate, hydrocarbylcarbonyloxy, nitro, halo, hydrocarbylsulfinyl, amino or hydrocarbylsulfonyl. More preferred substituents on the aryl radical include $C_{1-20}$ alkyl, halo, nitro or cyano. The most preferred substituents on the aryl moiety include $C_{1-3}$ alkyl, halo, nitro or cyano.

The cyclobutene ring may be substituted with electron-withdrawing groups, wherein electron-withdrawing groups are described hereinbefore. Preferred substituents on the cyclobutene ring are cyano, carboxylate, hydrocarbylcarbonyloxy, nitro, halo, hydrocarbylsulfonyl or hydrocarbylsulfinyl. More preferred substituents include halo, nitro or cyano groups; with cyano groups being most preferred.

The arylcyclobutene moieties and amido alkenoic acid moieties are connected herein by a direct bond or bridging member. Bridging members comprise (1) a polyvalent inorganic moiety, or (2) a polyvalent organic moiety. The bridging member or direct bond connects the arylcyclobutene moieties through the aryl radical to the amido alkenoic acid moieties through the amide nitrogen.

Polyvalent inorganic moiety refers to any inorganic moiety which is capable of bonding to an aryl radical and an amide nitrogen. Such polyvalent inorganic moieties can be covalently or ionically bonded to the aromatic radical and the amide nitrogen atom. Examples of polyvalent inorganic moieties include oxygen, phosphorus, phosphorus oxide, sulfur, nitrogen, polysiloxanes, polyvalent metals, sulfoxide, sulfone, a polyvalent metal bound to a polyvalent oxygenated moiety wherein the polyvalent oxygenated moiety can be further bound to an aryl radical (for example, a polyvalent carboxylate salt). Preferred polyvalent inorganic moieties include oxygen, sulfur, polysiloxanes, and polyvalent metals bound to polyvalent oxygenated moieties.

The polyvalent organic bridging member can be any polyvalent organic moiety which can link an aryl radical to an amide nitrogen.

Preferred bridging members are the divalent organic radicals which are bonded to the nitrogen of the amide and the aryl radical of the arylcyclobutene moiety. The divalent organic radical useful as a bridging member is any divalent organic radical which is capable of being bonded to both the nitrogen of an amide and an aryl radical. The divalent organic radical is preferably a hydrocarbylene, hydrocarbyleneamido, hydrocarbylenecarbonyloxy, hydrocarbyleneoxy, hydrocarbylenethio, hydrocarbylenesulfinyl or hydrocarbylenesulfonyl radical. More preferred divalent organic radicals are alkylene, arylene, alkylene-bridged polyarylene, cycloalkylene-bridged polyarylene, alkenylene-bridged polyarylene, alkyleneamido, aryleneamido, alkylene-bridged polyaryleneamido, cycloalkylene-bridged polyaryleneamido, alkenylene-bridged polyaryleneamido, alkylenecarbonyloxy, arylenecarbonyloxy, alkylene-bridged polyarylenecarbonyloxy, cycloalkylene-bridged polyarylenecarbonyloxy, alkenylene-bridged polyarylenecarbonyloxy, alkyleneoxy, aryleneoxy, alkylene-bridged polyaryleneoxy, cycloalkylene-bridged polyaryleneoxy, alkenylene-bridged polyaryleneoxy, alkylenethio, arylenethio, alkylene-bridged polyarylenethio, cycloalkylene-bridged polyarylenethio, alkenylene-bridged polyarylenethio, alkylenesulfinyl, arylenesulfinyl, alkylene-bridged polyarylenesulfinyl, cycloalkylene-bridged polyarylenesulfinyl, alkenylene-bridged polyarylenesulfinyl, alkylenesulfonyl, arylenesulfonyl, alkylene-bridged polyarylenesulfonyl, cycloalkylene-bridged polyarylenesulfonyl or alkenylene-bridged polyarylenesulfonyl. Even more preferred divalent organic radicals include alkylene, arylene, alkylenecarbonyloxy, arylenecarbonyloxy, alkyleneamido, aryleneamido, alkyleneoxy, aryleneoxy, alkylenethio or arylenethio. Most preferred divalent organic radicals include alkylene and arylene radicals.

Preferably, the aryl moiety and cyclic imide are connected by a direct bond or a bridging member which comprises an alkylene, arylene, alkylene-bridged polyarylene or cycloalkylene-bridged polyarylene; and more preferably a direct bond or a bridging member which comprises an alkylene or arylene moiety. Most preferably the amide nitrogen and the aryl radical are connected by a direct bond.

Preferred arylcyclobutenyl amido alkenoic acids or water-soluble salts thereof correspond to the formula

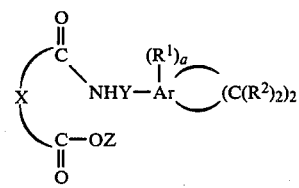

wherein
Ar is an aromatic radical;
$R^1$ is separately in each occurrence a hydrocarbyl, hydrocarbyloxy, hydrocarbylthio, electron-donating or electron-withdrawing group;

$R^2$ is separately in each occurrence hydrogen or an electron-withdrawing group;

X is an alkenylene moiety which can be substituted with one or more hydrocarbyl, hydrocarbyloxy or hydrocarbylthio groups;

Y is a direct bond or divalent organic moiety;

Z is hydrogen or a cation derived from ammonia, a primary or secondary amine, an alkali metal base or alkaline earth metal base; and a is an integer of between about 0 and 3.

More preferred arylcyclobutenyl amido alkenoic acids or water-soluble salts thereof include those which correspond to the formula $$R^3\underset{R^3}{\overset{}{\diagdown}}\underset{\underset{O}{\overset{}{\|}}}{\overset{\overset{O}{\|}}{C}}\underset{C}{\overset{}{\diagup}}\overset{NHY-Ar}{\underset{OZ}{}}\overset{(R^1)_a}{\underset{(C(R^2)_2)_2}{}}$$

wherein

Ar is an aromatic radical;

$R^1$ is separately in each occurrence a hydrocarbyl, hydrocarbyloxy, hydrocarbylthio, an electron-donating or electron-withdrawing group;

$R^2$ is separately in each occurrence hydrogen or an electron-withdrawing group;

$R^3$ is separately in each occurrence hydrogen, a hydrocarbyl, hydrocarbyloxy or hydrocarbylthio group;

Y is a direct bond or a divalent organic radical;

Z is hydrogen or a cation derived from ammonia, a primary or secondary amine, an alkali metal base or alkaline earth metal base; and a is an integer of between about 0 and 3.

In an even more preferred embodiment, the arylcyclobutenyl amido alkenoic acid or water-soluble salt thereof corresponds to the formula $$R^3\underset{R^3}{\overset{}{\diagdown}}\underset{\underset{O}{\overset{}{\|}}}{\overset{\overset{O}{\|}}{C}}\underset{C}{\overset{}{\diagup}}\overset{N-Y-}{\underset{OZ}{}}\overset{(R^1)_b}{\underset{}{\bigcirc}}\overset{(R^2)_2}{\underset{(R^2)_2}{}}$$

wherein $R^1$ is separately in each occurrence a hydrocarbyl, hydrocarbylthio, hydrocarbyloxy, electron-withdrawing or electron-donating group;

$R^2$ is separately in each occurrence hydrogen or an electron-withdrawing group;

$R^3$ is separately in each occurrence hydrogen, hydrocarbyl, hydrocarbyloxy or hydrocarbylthio;

Y is a direct bond or a divalent organic radical;

Z is hydrogen or a cation derived from ammonia, a primary or secondary amine, an alkali metal base or alkaline earth metal base; and b is an integer of between 0 and 3, inclusive.

In the above formulas, $R^1$ is preferably $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ alkaryl, $C_{7-20}$ alkaryloxy, $C_{7-20}$ alkarylthio, $C_{7-20}$ aralkyl, $C_{7-20}$ aralkoxy, $C_{7-20}$ aralkylthio, cyano, carboxylate, hydrocarbylcarbonyloxy, nitro, halo, hydrocarbylsulfinyl, hydrocarbylsulfonyl or amino, $R^1$ is more preferably $C_{1-20}$ alkyl, halo, nitro or cyano. Most preferably $R^1$ is $C_{1-3}$ alkyl, halo, nitro or cyano.

$R^2$ is preferably hydrogen, cyano, carboxylate, hydrocarbylcarbonyloxy, nitro, halo, hydrocarbylsulfonyl or hydrocarbylsulfinyl. $R^2$ is more preferably hydrogen, halo, nitro or cyano. $R^2$ is even more preferably hydrogen or cyano and most preferably hydrogen.

$R^3$ is preferably hydrogen, $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ alkaryl, $C_{7-20}$ alkaryloxy, $C_{7-20}$ alkarylthio, $C_{7-20}$ aralkyl, $C_{7-20}$ aralkoxy or $C_{7-20}$ aralkylthio. $R^3$ is more preferably hydrogen or $C_{1-20}$ alkyl. $R^3$ is even more preferably hydrogen or $C_{1-3}$ alkyl and most preferably hydrogen.

In the above formulas, Y is preferably a direct bond, a hydrocarbylene, hydrocarbyleneamido, hydrocarbylenecarbonyloxy, hydrocarbyleneoxy, hydrocarbyleneamino, hydrocarbylenecarbonyl, hydrocarbylenethio, hydrocarbylenepolythio, hydrocarbylenesulfinyl or hydrocarbylenesulfonyl. Y is more preferably a direct bond, alkylene, arylene, alkylene-bridged polyarylene, cycloalkylene-bridged polyarylene, alkyleneamido, aryleneamido, alkylenecarbonyloxy, arylenecarbonyloxy, arylenecarbonyl, alkylenecarbonyl, aryleneoxy, alkyleneoxy, aryleneamino, alkyleneamino, alkylenethio, alkylenepolythio, arylenethio, arylenepolythio, arylenesulfinyl, alkylenesulfinyl, arylenesulfonyl or alkylenesulfonyl. Y is most preferably a direct bond, alkylene or arylene.

In the above formulas, Z is preferably hydrogen, a cation derived from ammonia, an alkali metal base, an alkaline earth metal base, or an amine. More preferred cations are those derived from ammonia, an alkali metal base, or an amine. Even more preferred cations are $(R^6)_a N^{\oplus}(H)_b$ wherein $R^6$ is $C_{1-10}$ alkyl or $C_{1-10}$ aryl; a is 0 to 3; b is 1 to 4; with the proviso that a+b=4. The most preferred cation is an ammonium ion.

In the formulas described hereinbefore, Ar is preferably a benzene, naphthalene, phenanthrene, anthracene or biaryl radical, or two or more aromatic radicals bridged by alkylene moieties. Ar is more preferably benzene, naphthalene, biphenyl, binaphthyl or a diphenylalkylene. Ar is more preferably a benzene radical.

Hydrocarbyl means herein an organic radical containing carbon and hydrogen atoms. The term hydrocarbyl includes the following organic radicals: alkyl, alkenyl, alkynyl, cycloalkyl, cycloalkenyl, aryl, aliphatic, and cycloaliphatic aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to biaryl, biphenylyl, phenyl, naphthyl, phenanthranyl, anthranyl and two aryl groups bridged by an alkylene group or alkenylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. $C_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-5}$ alkyl includes methyl, ethyl, propyl, butyl and pentyl.

Cycloalkyl refers to alkyl groups containing one, two, three or more cyclic rings. Cycloalkenyl refers to mono-, di- and polycyclic groups containing one or more double bonds. Cycloalkenyl also refers to cycloalkenyl groups wherein two or more double bonds are present.

Hydrocarbylene herein refers to a divalent radical containing carbon and hydrogen atoms and is analogous to the hydrocarbyl radicals described hereinbefore with the single difference that the hydrocarbylene radical is divalent.

Hydrocarbyleneamido refers herein to a divalent radical wherein a hydrocarbylene radical is bonded to an amido group, and corresponds to the formula

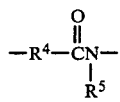

wherein $R^4$ is a hydrocarbylene radical and $R^5$ is hydrogen or a hydrocarbyl radical.

Hydrocarbyleneoxy refers herein to a divalent radical in which a hydrocarbylene radical is bonded to a divalent oxygen atom and corresponds to the formula —$R^4$—O— wherein $R^4$ is as defined hereinbefore.

Hydrocarbylenecarbonyloxy refers to a hydrocarbylene moiety which is bonded to a carbonyl moiety which is further bonded to a divalent oxygen atom and corresponds to the formula

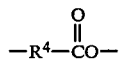

wherein $R^4$ is as defined hereinbefore.

Hydrocarbyleneoxycarbonyl refers to a hydrocarbylene moiety which is bonded to a divalent oxygen atom, wherein the oxygen atom is further bonded to a carbonyl moiety and corresponds to the formula

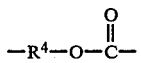

wherein $R^4$ is as hereinbefore defined.

Hydrocarbylenethio refers herein to a radical in which a hydrocarbylene radical is further bonded to one or more sulfur moieties and corresponds to the formula —$R^4$—$(S)_p$— wherein $R^4$ is as hereinbefore defined, and wherein p is between 1 and 3.

Hydrocarbyleneamino refers herein to a hydrocarbylene radical bonded to an amino moiety and generally corresponds to the formula

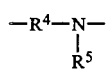

wherein $R^4$ and $R^5$ are as defined hereinbefore.

Hydrocarbylenesulfinyl refers herein to a hydrocarbylene moiety bonded to a sulfinyl moiety and generally corresponds to the formula

wherein $R^4$ is as hereinbefore defined.

Hydrocarbylenesulfonyl generally corresponds to a radical in which a hydrocarbylene radical is bonded to a sulfonyl radical and corresponds to the formula

wherein $R^4$ is as hereinbefore defined.

Wherein the bridging member is a hydrocarbyleneamido, hydrocarbyleneoxy, hydrocarbyleneamino, hydrocarbylenethio, hydrocarbylenecarbonyloxy moiety, the amido, amino, oxy, thio, sulfinyl or sulfonyl moiety is preferably bonded to the aryl portion of the arylcyclobutene.

Alkylene-bridged polyarylene, alkenylene-bridged polyarylene and cycloalkylene-bridged polyarylene refers herein to divalent radicals containing two or more arylene moieties wherein the arylene moieties are connected by alkylene, alkenylene or cycloalkylene moieties (bridges), respectively. In one preferred embodiment, such bridging members generally correspond to the formula

wherein Ar is as hereinbefore defined; $R^{11}$ is separately in each occurrence an alkylene, cycloalkylene or alkenylene radical; r is independently in each occurrence 0 or 1; and q is 1 or greater. $R^{11}$ is preferably a $C_{1-20}$ alkylene or $C_{1-20}$ alkenylene. $R^{11}$ is more preferably $C_{1-10}$ alkylene or $C_{1-10}$ alkenylene. $R^{11}$ is even more preferably $C_{1-4}$ alkylene or $C_{1-4}$ alkenylene, with —CH=CH— being most preferred. Preferably q is between 1 and 20, most preferably between 1 and 10. In a more preferred embodiment, the aromatic radical hydrocarbon poly-yl bridging member corresponds to the formula

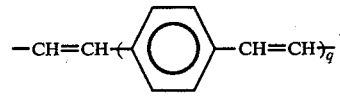

wherein q is as hereinbefore defined.

Examples of preferred arylcyclobutenyl amido alkenoic acids include N-benzocyclobutenylmethyl amido butenoic acid, N-benzocyclobutenylethyl amido butenoic acid, N-[(bicyclo(4.2.0)octa-1,3,5-trien-3-ylamino)methyl]maleamic acid, N-benzocyclobutenylpropyl amido butenoic acid, N-benzocyclobutenylbutyl amido butenoic acid, N-benzocyclobutenylhexyl amido butenoic acid, N-benzocyclobutenylphenyl amido butenoic acid, N-benzocyclobutenylbiphenyl amido butenoic acid, N-benzocyclobutenylamidomethyl amido butenoic acid, N-[bicyclo(4.2.0)octa-1,3,5-trien-3-ylamino]-2-oxoethyl]maleamic acid, N-benzocyclobutenylamidoethyl amido butenoic acid, N-benzocyclobutenylamidopropyl amido butenoic acid, N-benzocyclobutenylamidobutyl amido butenoic acid, N-benzocyclobutenylamidopentyl amido butenoic acid, N-benzocyclobutenylamidohexyl amido butenoic acid, N-benzocyclobutenylamidophenyl amido butenoic acid, N-benzocyclobutenylamidobiphenyl amido butenoic acid, N-benzocyclobutenyloxycarbonylmethyl amido butenoic acid, N-[(bicyclo(4.2.0)octa-1,3,5-trien-3-yloxy]-z-oxoethyl]maleamic acid, N-benzocyclobutenyloxycarbonylethyl amido butenoic acid, N-benzocyclobutenyloxycarbonylpropyl amido butenoic acid, N-benzocyclobutenyloxycarbonylbutyl amido butenoic acid, N-benzocyclobutenyloxycarbonylpentyl amido butenoic acid, N-benzocyclobutenyloxycarbonylhexyl amido butenoic acid, N-benzocyclobutenyloxycarbonylphenyl amido butenoic acid, N-benzocyclobutenyloxycarbonylbiphenyl amido butenoic acid, N-benzocyclobutenylthiomethyl amido butenoic acid, N-benzocyclobutenylthioethyl amido butenoic acid, N-[2-(bicyclo(4.2.0)octa-1,3,5-trien-3-ylthio)ethyl]maleamic acid, N-benzocyclobutenylthiopropyl amido butenoic acid, N-benzocyclobutenylthiobutyl amido butenoic acid, N-benzocyclobutenylthiopentyl amido butenoic acid, N-benzocyclobutenylthiohexyl amido butenoic acid, N-benzocyclobutenylthiophenyl amido butenoic acid, N-benzocyclobutenylthiobiphenyl amido butenoic acid, N-benzocyclobutenyloxymethyl amido butenoic acid, N-benzocyclobutenyloxyethyl amido butenoic acid, N-[2-(bicyclo(4.2.0)octa-1,3,5-trien-3-yloxy)ethyl]maleamic acid, N-benzocyclobutenyloxypropyl amido butenoic acid, N-benzocyclobutenyloxybutyl amido butenoic acid, N-benzocyclobutenyloxypentyl amido butenoic acid, N-benzocyclobutenyloxyhexyl amido butenoic acid, N-benzocyclobutenyloxyphenyl amido butenoic acid, N-benzocyclobutenyloxybiphenyl amido butenoic acid, and the like.

The arylcyclobutene moieties can be prepared by several synthesis schemes.

In one synthesis scheme, an alkyl-substituted aromatic compound which is further substituted with an aryl deactivating substituent is chloroalkylated in a position ortho to the alkyl group. In the preferred embodiment wherein the aromatic compound is benzene, the starting material corresponds to the following formula

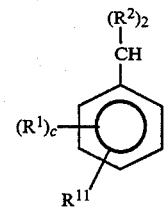

wherein $R^1$ and $R^2$ are as defined hereinbefore; $R^{11}$ is any aryl deactivating substituent; and c is an integer of 0, 1, 2, or 3. The alkyl N-substituted aromatic compound is chloroalkylated by contacting the alkyl aromatic compound with a chloroalkylating agent and thionyl chloride in the presence of an iron chloride catalyst so as to result in a product which contains a chloroalkyl group ortho to the alkyl substituent. In the embodiment wherein the aromatic compound is a benzene ring, the product corresponds to the formula

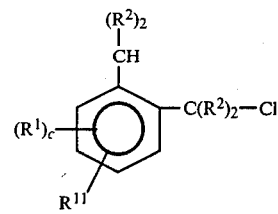

wherein $R^{11}$ is a hydrocarbyloxycarbonyl, carboxamide, hydrocarbylcarbonyl, carboxylate, halocarbonyl, nitrile, nitro, sulfone or sulfoxide group. $R^{11}$ is more preferably a halo or hydrocarbyloxycarbonyl group, with hydrocarbyloxycarbonyl being the most preferred group. Preferably c is 0 or 1, most preferably 0.

In this process the chloroalkylating agent is preferably chloromethyl methyl ether, although other chloroalkylating agents such as bis(chloromethyl)ether could be used. At least a 2:1 molar excess of the chloroalkylating agent to the alkyl-substituted aromatic compound is needed. It is preferable to use between about a 6:1 and 3:1 ratio of chloroalkylating agent to alkyl aromatic compound. The catalyst is ferric chloride (FeCl$_3$) while the cocatalyst is thionyl chloride. The catalyst can be present in between about 0.1 and 1.0 mole per mole of alkyl aromatic. More preferably between about 0.2 and 0.4 mole of catalyst are present for each mole of alkyl aromatic compound. Preferably between about 0.1 and 1.0 mole of thionyl chloride per mole of alkyl aromatic is used, more preferably between about 0.2 and 0.4 mole per mole of alkyl aromatic.

This process can be performed at a temperature of between about 40° C. and 80° C., preferably about 40° C. and 60° C. Below about 40° C., the reaction rate is low. The boiling point of some of the components of the reaction mixture starts at about 80° C.

This process can be done by contacting the alkyl aromatic compound with the chloromethylating agent, catalyst and cocatalyst in a suitable solvent. Suitable solvents include chlorinated hydrocarbon solvents. Thereafter the reaction mixture is heated to the appropriate temperature.

The product can be recovered by quenching the reaction mixture with alcohols or water to inactivate the chloroalkylating agents remaining, stripping off the volatiles and washing out the catalyst with water. The product thereafter is recovered by distillation.

The ortho chloroalkylated alkyl aromatic compounds can be converted to aromatic compounds with cyclobutene rings fused thereto, by pyrolysis. This is achieved by contacting the ortho chloroalkylated alkyl aromatic compound with at least 2 times its weight of a suitable diluent, and thereafter passing the mixture through a reactor at a temperature of 550° C. or greater and a pressure of between about atmospheric and 25 mm of mercury. Suitable diluents are generally substituted aromatic compounds which are inert to the chloromethylated alkyl aromatic compound and are stable at pyrolysis temperatures. Examples of suitable diluents are benzene, toluene, xylenes, chlorobenzenes, nitrobenzenes, methylbenzoates, phenyl acetate or diphenyl acetate. Preferred diluents are the xylenes. Preferable temperatures are between about 700° C. and 750° C. Preferable pressures are between about 35 and 25 mm of mercury. In a preferred embodiment, the reaction mixture is passed through a hot tube packed with an inert material, for example, quartz chips or stainless steel helices. The product can be recovered by distillation. The product wherein the aromatic compound is benzene corresponds to the formula

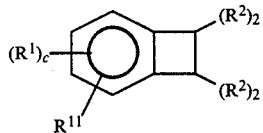

wherein $R^1$, $R^2$, $R^{11}$ and c are as hereinbefore defined.

In the preferred embodiment wherein $R^{11}$ is a hydrocarbyloxy carbonyl moiety, the hydrocarbyloxy carbonyl moiety can be converted to a carboxylate moiety by contacting the substituted (arylcyclobutene) compound with at least a molar equivalent of alkali metal hydroxide in an alkanol-water solvent system. In the embodiment wherein the aromatic radical is benzene, the product corresponds to the formula

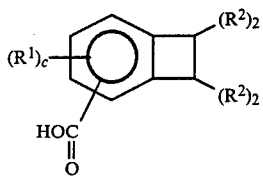

Thereafter the carboxylate-substituted (arylcyclobutene) compound can be converted to an acid chloride by contacting the carboxylate-substituted (arylcyclobutene) compound with thionyl chloride and refluxing at 70° C. to 80° C. The acid halide-substituted (arylcyclobutene) so formed can be used to prepare the novel monomers of this invention, as described hereinafter. In the embodiment wherein the aryl radical is a benzene ring, the product corresponds to the formula

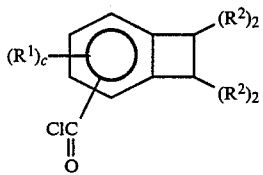

In an alternative synthesis, an aryl compound with ortho dibromomethyl groups can be converted to a 1,2-diiodoarylcyclobutene, by contacting the aryl compound substituted with ortho dibromomethyl moieties with an alkali metal iodide in an alkanol solvent at reflux so as to form the diiodoarylcyclobutenes. The product can be recovered by filtering, evaporating the filtrate and recrystallizing the product. In the embodiment wherein the aryl radical is a benzene radical, the starting material corresponds to the formula

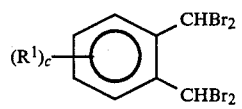

and the iodobenzocyclobutene corresponds to the formula

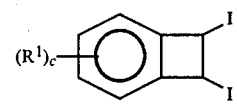

The 1,2-diiodoarylcyclobutenes can be converted to dehalogenated arylcyclobutenes by dissolving the 1,2-diiodoarylcyclobutenes in an alcohol solvent, preferably methanol or ethanol and contacting the solution with an alkali metal hydroxide in the presence of a palladium-on-carbon catalyst and $H_2$ gas at a temperature of 20° C. to 30° C. In general, at least between about 2 and 4 moles of alkali metal hydroxide per mole of 1,2-diiodoarylcyclobutene is used. Preferably, between about 50 and 200 psi of hydrogen gas is used. The arylcyclobutenes prepared in this manner can be recovered by distillation. In the embodiment wherein the aryl radical is a benzene radical, the product corresponds to the formula

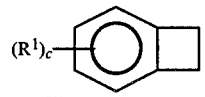

The arylcyclobutene is thereafter brominated. In this process, the arylcyclobutene is dissolved in acetic acid and contacted with a brominating agent of pyridinium hydrobromide perbromide in the presence of mercuric salts, for example, mercuric acetate, at a temperature of between about 20° C. and 50° C. The brominated product can be recovered by extraction and distillation. In the embodiment wherein aryl radical is benzene, the product corresponds to the formula

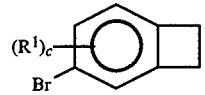

The brominated arylcyclobutene can thereafter be carbonylated to prepare a hydrocarbyloxy carbonyl-substituted arylcyclobutene. This carbonylation is achieved by dissolving the brominated arylcyclobutene in an alkanol solvent, and thereafter contacting the solution with carbon monoxide under pressure in the presence of a palladium catalyst, wherein the palladium is in the zero valence state, in the further presence of an acid acceptor under conditions such that the brominated arylcyclobutene compound undergoes carbonylation. Preferred catalysts are palladium acetate with a cocatalyst of triphenyl phosphine, palladium triphenyl phosphine tetrakis, and bis(triphenyl phosphine)palladium chloride complex. The acid acceptor is generally a tertiary amine. In general, the reaction vessel is pressurized with carbon monoxide to a pressure of between atmospheric and 3000 psi, preferred pressures are between 600 and 1000 psi.

This process is preferably run at a temperature of between 100° C. and 140° C., most preferably between 120° C. and 130° C. The hydrocarbyloxycarbonyl arylcyclobutene can be recovered by filtering off the catalyst, washing away the acid scavenger with a 10 percent strong acid solution, stripping off the solvent and distilling the product to purify it. To prepare a carboxamide-substituted arylcyclobutene, a primary or secondary amine is substituted for the alcohol solvent. In the embodiment wherein the aryl radical is a benzene radical, the process corresponds to the following equation:

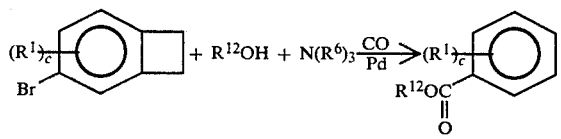

wherein R and c are as hereinbefore defined and $R^1$, $R^6$ and $R^{12}$ are hydrocarbyl moieties. The hydrocarbyloxycarbonyl-substituted or carboxamide-substituted arylcyclobutenes can thereafter be acidified and converted to acid chlorides by the process described hereinbefore.

In another preparation of an arylcyclobutene, the reaction may follow that reported by Skorcz and Kaminski, *Org. Syn.*, 48, pages 53–56 (1968). In a typical preparation, an alkyl cyanoacetate is added to a solution of sodium metal in ethanol followed by the addition of an ortho-halomethylaryl halide. The alkyl 2-(O-halomethylaryl)cyanoacetate is isolated and treated with aqueous sodium hydroxide. Subsequent acidification results in the cyanoacetic acid derivative. That derivative is placed into N,N-dimethylformamide and is refluxed to form the 3-(O-halomethylaryl)propionitrile derivative which is isolated and added to a suspension of sodamide in liquid ammonia. After an appropriate reaction time, ammonium nitrate is added and the ammonia allowed to evaporate. The cyanoarylcyclobutene is isolated by ether extraction and purified by fractional distillation under reduced pressure.

Substituted arylcyclobutenes can be prepared by the same technique by using the appropriately substituted reactants, such as an alkyl or alkoxybenzyl halide. Also substituents can result from using an alkyl haloacetate or a dialkylmalonate.

In another preparation based on the paper by Matsura et al., *Bull. Chem. Soc. Jap.*, 39, 1342 (1966), o-aminoaryl carboxylic acid is dissolved in ethanol and hydrochloric acid added. Isoamylnitrite is slowly added to the cold stirred solution and diethyl ether is then added. The product, aryldiazonium-2-carboxylate hydrochloride, is filtered. That product is placed in a solvent, preferably ethylene dichloride, and acrylonitrile and propylene oxide is added to the stirred mixture which is then heated under nitrogen until the reaction is complete. After cooling, the mixture is filtered and the product, 1-cyanoarylcyclobutene, is isolated by fractionally distilling the filtrate under reduced pressure.

Amounts of reactants, reaction parameters and other details can be found in the cited article, the examples of this application, or can be easily deduced therefrom.

In a next sequence of reactions, the cyanoarylcyclobutene or substituted derivative is nuclear substituted. In one preparation, the cyanoarylcyclobutene is added slowly to a cold solution of sodium nitrate is concentrated sulfuric acid to form 5-nitro-1-cyanoarylcyclobutene. That nitro compound is isolated, dissolved in ethanol and reduced by hydrogenation over a palladium on carbon catalyst. The isolated product is 5-amino-1-cyanoarylcyclobutene. In the preferred embodiment where the aryl radical is benzene, the product corresponds to the formula

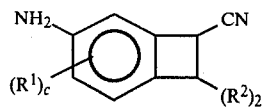

The formation of the arylcyclobutenyl amido alkenoic acid is achieved by reacting an unsaturated cyclic anhydride with an amine-substituted arylcyclobutene. The cyclic anhydride corresponds to the formula

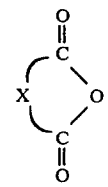

and the amine-substituted arylcyclobutene corresponds to the formula

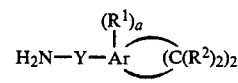

wherein
Ar is an aromatic radical;
$R^1$ is separately in each occurrence a hydrocarbyl, hydrocarbyloxy, hydrocarbylthio, an electron-donating or electron-withdrawing group;
X is an alkylene moiety which can be substituted with one or more hydrocarbyl, hydrocarbyloxy or hydrocarbylthio groups;
Y is a direct bond or a divalent organic radical; and
a is an integer of between about 0 and 3.
This process is exemplified by the following equation

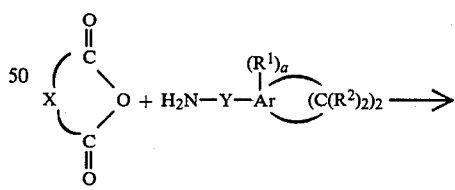

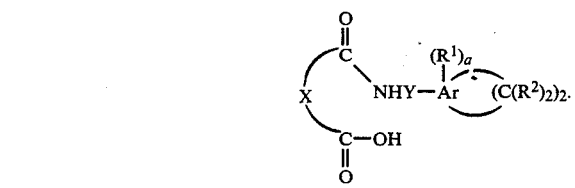

This reaction is exemplified in one preferred embodiment wherein the anhydride is maleic anhydride and the arylcyclobutene is 4-aminobenzocyclobutene, and is illustrated by the following equation:

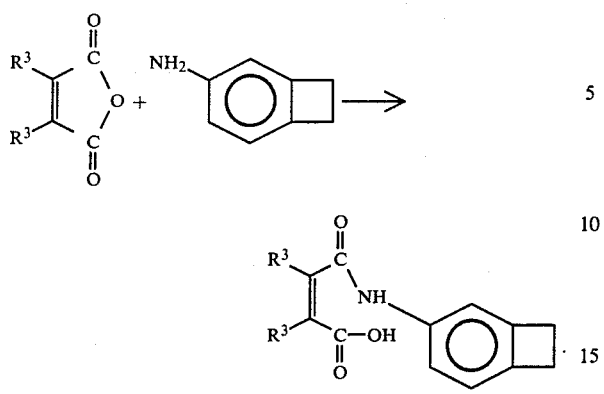

The cyclic anhydride and amino-substituted arylcyclobutene are contacted in a suitable solvent at a temperature of between −40° C. and 100° C. Suitable solvents include aliphatic hydrocarbons, aromatic hydrocarbons, ethers and halogenated hydrocarbons. It is preferred to run the process under an inert atmosphere. It is also preferred to use freshly sublimed anhydride as any impurities in the anhydride can result in very poor yields. It is also preferred to use at least a 5 percent excess of anhydride so as to drive the reaction to completion with respect to the amino-substituted arylcyclobutene compound.

Preferred temperatures are between 0° C. and 50° C. with between 20° C. and 25° C. being most preferred.

The N-arylcyclobutenyl amido alkenoic acid can be dehydrated by one of two methods. In the preferred embodiment, the N-arylcyclobutenyl amido alkenoic acid is contacted with a dehydrating agent in an aprotic reaction medium in the presence of a nickel II salt catalyst. In general, the reaction medium is an aprotic solvent and can include ketones, ethers, amides or aliphatic halogenated hydrocarbons. Preferred reaction media include the ketones, with acetone being most preferred. The dehydrating agents include anhydrides, carbodiimides, and isocyanates; with the anhydrides being preferred and acetic anhydride being most preferred.

The catalyst is any nickel II salt with nickel II acetate being most preferred. In general, between about 1 and 5 percent of the catalyst is useful. It is preferable to run this process in the presence of an aprotic base such as a carbonate or tertiary amine, preferably a tertiary amine. In general, between about 20 and 200 mole percent of a tertiary amine is used, with between about 100 and 150 mole percent being preferred, wherein mole percentages are based on the starting N-arylcyclobutenyl amido alkenoic acid. The mole ratio of the dehydrating agent to the N-arylcyclobutenyl amido alkenoic acid is between about 4:1 and 1:1, preferably between about 1.5:1 and 1:1.

It is preferred to run this process under an inert atmosphere. Temperatures which are useful are those at which the dehydration takes place. Preferable temperatures are between about −20° C. and 100° C., with between about 15° C. and 25° C. being most preferred.

In this reaction, the N-arylcyclobutenyl amido alkenoic acid is often not soluble in the reaction medium but the cyclic imide product is. The reactant is slurried in the reaction media and exposed to the reaction conditions described. The completion of the reaction is noted by dissolution of the reactants indicating formation of products.

In an alternative procedure, the N-arylcyclobutenyl amido alkenoic acid can be dehydrated by dispersing the compound in a glacial acetic acid reaction media in the presence of an alkali or alkaline earth metal acetate salt, and heating the reaction mixture to a temperature at which the dehydration takes place to form the cyclic imide rings. Generally, a sufficient amount of alkali or alkaline earth metal acetate salt to cause complete dehydration is suitable. Preferably, at least an equimolar amount of alkali or alkaline earth metal acetate salt is used, most preferably an excess of 5 mole percent. The process can be run at any temperature at which the dehydration takes place, preferable temperatures are between 50° C. and 140° C., with between about 100° C. and 120° C. being most preferred. Completion of the reaction is indicated by dissolution of the product.

In both instances, the product can be recovered by washing with water and thereafter an aqueous solution of an inorganic base.

The precursor for the hydrocarbylene amino-bridged arylcyclobutenyl amido alkenoic acid can be prepared by the following procedure. An amino-substituted arylcyclobutene is reacted with about an equimolar amount of a hydrocarbon substituted with aldehyde and nitro moieties, in the presence of between about 0.3 to 1.5 moles of sodium cyanoborohydride in a methanolic solvent at about 20° C. to about 25° C. The product is nitrohydrocarbylamino-substituted arylcyclobutene. The process can be exemplified by the following equation

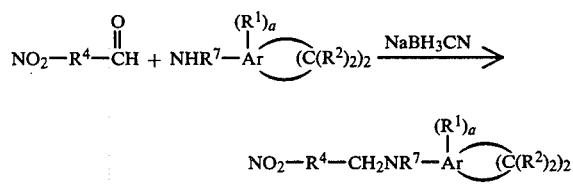

wherein $R^4$ is hydrocarbylene and $R^7$ is hydrogen or a hydrocarbyl moiety. The nitro moiety on the nitrohydrocarbylamino-substituted arylcyclobutene is reduced to an amine moiety by contacting with an excess of metallic zinc in a concentrated hydrochloric acid solution at between about 20° C. and reflux, or alternatively, by hydrogenation in ethonal over a palladium catalyst at about 25° C. and about 50 psi. The product corresponds to the formula

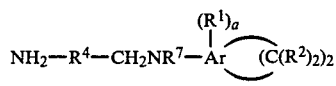

wherein $R^4$ is as hereinbefore defined. The aminohydrocarbyl amino-substituted arylcyclobutene is thereafter reacted with a cyclic anhydride to prepare a hydrocarbylene amino-bridged N-arylcyclobutenyl amido alkanoic acid. The conditions for this reaction are as described hereinbefore for the reaction of an amino-substituted arylcyclobutene and a cyclic anhydride. This reaction is exemplified by the following equation

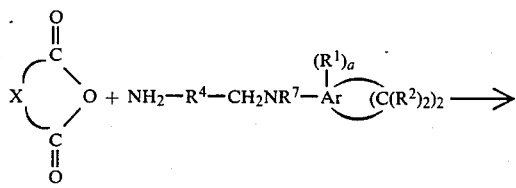

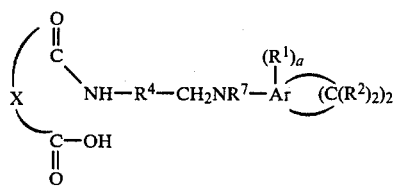

A hydrocarbylene-bridged arylcyclobutenyl amido alkenoic acid can be prepared by the following procedure. A carboxy-substituted or carboxyhydrocarbyl-substituted arylcyclobutene is reduced to a hydroxyhydrocarbyl-substituted arylcyclobutene by reacting the starting material with about a 3:1 molar excess of diborane, or 2:1 molar excess of lithium aluminum hydride, in an ether or cyclic ether solvent at between about 0° C. to 20° C. This process is exemplified by the following equation

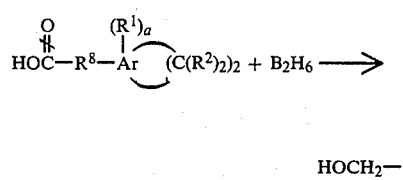

wherein $R^8$ is a direct bond or a hydrocarbylene moiety. The hydroxyhydrocarbyl-substituted arylcyclobutene is reacted with a slight excess of thionyl chloride to prepare a chlorohydrocarbyl-substituted arylcyclobutene. The reactants are usually contacted neat or in a methylene chloride solvent at a temperature of between about 0° C. and 50° C. An example of the product corresponds to the formula

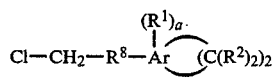

The chlorohydrocarbyl-substituted arylcyclobutene is thereafter reacted with about an equimolar amount of potassium phthalimide to prepare an N-arylcyclobutenylhydrocarbyl phthalimide. The reactants are generally contacted neat at temperatures of between about 100° C. and 200° C. This reaction is exemplified by the following equation

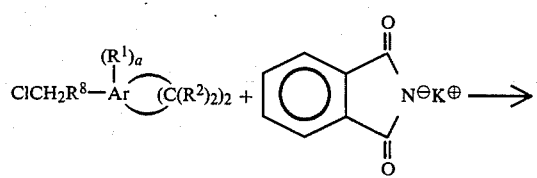

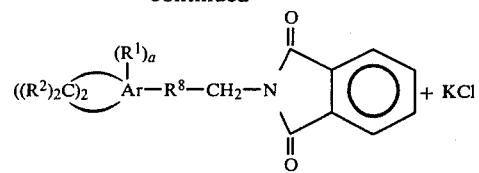

wherein $R^8$ is as hereinbefore defined. The N-arylcyclobutenylhydrocarbyl phthalamide is reacted with about one equivalent of hydrazine hydrate to prepare an aminohydrocarbyl-substituted benzocyclobutene. The reactants are contacted in an alkanol solvent at the reflux of the solvent. The product corresponds to the formula

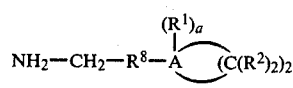

wherein $R^8$ is as hereinbefore defined. The aminohydrocarbyl-substituted benzocyclobutene is thereafter reacted with an unsaturated cyclic anhydride to prepare an N-hydrocarbylarylcyclobutenyl amido alkenoic acid under the conditions described hereinbefore. This process is exemplified by the following equation

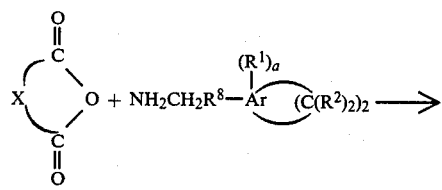

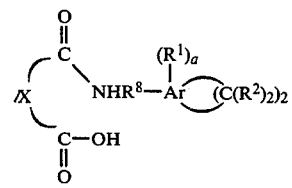

wherein $R^3$ and $R^8$ are as hereinbefore defined.

An alternative process for preparing a propylene-bridged arylcyclobutenyl amido alkenoic acid is described by the following procedure. A hydroxymethyl-substituted arylcyclobutene is reacted with a six molar excess of chromium trioxide pyridine complex in methylene chloride solvent at about 25° C. to prepare an arylcyclobutene carboxaldehyde. The arylcyclobutene carboxaldehyde can thereafter be reacted with a molar equivalent of carboethoxy methylene triphenyl phosphorane in tetrahydrofuran solvent at 0° C. and then thereafter 60° C., to prepare ethyl-3-(arylcyclobutenyl)-propenoate. The ethyl-3-(arylcyclobutenyl)propenoate is thereafter reacted with excess hydrogen gas over a palladium metal catalyst of 2 weight percent on a support in an ethanol solvent at 25° C. to prepare ethyl-3-(arylcyclobutenyl)propanoate. The ethyl-3-(arylcyclobutenyl)propanoate can thereafter be reacted with a 2 molar excess of lithium aluminum hydride in a tetrahydrofuran solvent at about 65° C. to prepare a 3-hydroxypropylarylcyclobutene. The 3-hydroxypropylarylcyclobutene can thereafter be reacted with at least a 10 percent molar excess of thionyl bromide at 60°

C. to prepare 3-bromopropylarylcyclobutene. The 3-bromopropylarylcyclobutene is thereafter reacted with a molar equivalent of sodium nitrite in N,N-dimethylformamide solvent at 20° C. to prepare 3-nitropropylarylcyclobutene. The 3-nitropropylarylcyclobutene is thereafter hydrogenated using excess hydrogen gas over a palladium metal catalyst in ethanol solvent at 25° C. to prepare a 3-aminopropylarylcyclobutene. The 3-aminopropylarylcyclobutene can thereafter be reacted with a molar equivalent of an anhydride as described hereinbefore to prepare the propylene-bridged arylcyclobutenyl amido alkenoic acid.

An alternative method for preparing an ethylene-bridged arylcyclobutenyl amido alkenoic acid is described by the following procedure. A bromo-substituted arylcyclobutene is reacted with a molar excess of ethylene in the presence of a palladium acetate catalyst, about 0.05 mole is preferable, to prepare a vinyl-substituted arylcyclobutene. The vinyl-substituted arylcyclobutene is thereafter reacted with a molar equivalent of a borane tetrahydrofuran complex at 0° C. followed by addition of hydrogen peroxide and sodium hydroxide to prepare a 2-hydroxyethylarylcyclobutene. The 2-hydroxyethylarylcyclobutene is thereafter reacted with at least a 10 percent molar excess of thionyl chloride at 70° C. to prepare a 2-chloroethylarylcyclobutene. The 2-chloroethylarylcyclobutene is thereafter reacted with a 10 percent molar excess of potassium phthalimide in the presence of about 0.6 mole of potassium carbonate at 150° C.-200° C. to prepare a compound which corresponds to the formula

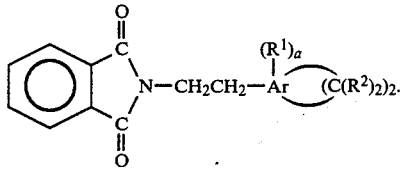

Such compound is thereafter reacted with a 10 percent molar excess of hydrazine hydrate to prepare 2-aminoethylarylcyclobutene. The 2-aminoethylarylcyclobutene can thereafter be reacted with a cyclic anhydride to prepare the ethylene-bridged arylcyclobutenyl amido alkenoic acid as described hereinbefore. An alternative procedure for preparing a 2-aminoethylarylcyclobutene involves reacting a vinyl-substituted arylcyclobutene with 1 mole of a borane tetrahydrofuran complex in tetrahydrofuran at 0° C. and thereafter contacting the reaction product with 2 equivalents of hydroxylamine-O-sulfonic acid to prepare the 2-aminoethylarylcyclobutene.

To prepare a mercaptoarylcyclobutene, an arylcyclobutene sulfonic acid and equimolar amounts of sodium hydroxide are contacted in aqueous solution at about 20° C.-25° C. to prepare sodium arylcyclobutene sulfonate. The sodium arylcyclobutene sulfonate is dried at 100° C., and thereafter contacted in neat form with about 0.48 mole of phosphorous pentachloride at about 170° C. to 180° C. to prepare an arylcyclobutene sulfonyl chloride. The arylcyclobutene sulfonyl chloride is reduced with zinc, about 4.9 moles, in the presence of about 6.8 moles of concentrated sulfuric acid at about 0° C. to prepare the mercaptoarylcyclobutene.

To prepare the alkylenethio-bridged arylcyclobutenyl amido alkenoic acid, equimolar amounts of a mercaptoarylcyclobutene, sodium hydroxide and a dihaloalkane are contacted in an alkanol solvent at between about 0° C. and 50° C. The product is a haloalkyl-substituted arylcyclobutenyl sulfide. This reaction is exemplified by the following equation

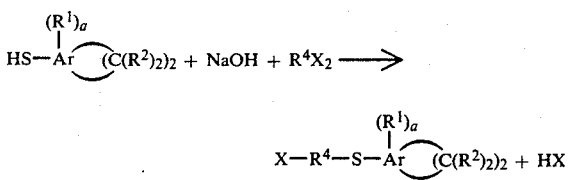

wherein X is halogen and $R^4$ is a divalent alkane radical. Two moles of the haloalkyl-substituted arylcyclobutenyl sulfide is contacted with about 0.8 moles of potassium phthalimide and about 0.4 mole of potassium carbonate. The reactants are contacted neat at a temperature of about 190° C. to prepare an n-phthalimidoalkylarylcyclobutenyl sulfide. This process is exemplified by the following equation

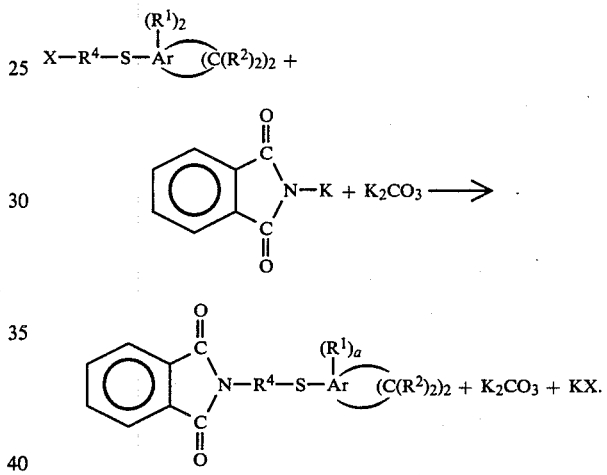

The phthalimidoalkylarylcyclobutenyl sulfide is contacted with a hydrazine hydrate in a mole ratio of about 1 to 1.25, respectively, in an alkanol solvent at reflux to prepare an aminoalkyl arylcyclobutenyl sulfide. In one preferred embodiment, the product corresponds to the formula

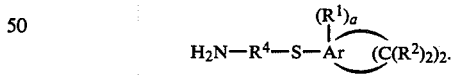

The aminoalkylarylcyclobutenyl sulfide is then reacted with a cyclic anhydride to prepare a thioalkylene-bridged N-arylcyclobutenyl amido alkenoic acid. This is achieved under conditions described hereinbefore.

The thiopropylene-bridged arylcyclobutenyl amido alkenoic acid can alternatively be prepared by the following process. One mole of mercaptoarylcyclobutene is reacted with about 1 mole of ethylacrylate in toluene at about 25° C. to prepare 2-(carboethoxy)ethylsulfide-substituted arylcyclobutene. The 2-(carboethoxy)ethylsulfide-substituted arylcyclobutene is thereafter contacted with 2 moles of lithium aluminum hydride in tetrahydrofuran at about 65° C. to prepare a 3-hydroxypropylsulfidearylcyclobutene. The 3-hydroxypropylsulfidearylcyclobutene is thereafter reacted with 1 mole of p-toluene sulfonyl chloride in the presence of 1 mole of a trialkylamine in methylene chloride solvent at 0° C. then at 20° C. to prepare toluene sulfonate propylsulfidearylcyclobutene, which product corresponds to the formula

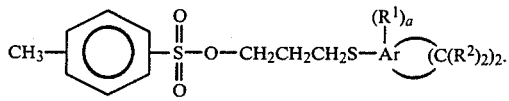

This compound is thereafter reacted with a 10 mole percent excess of potassium phthalimide in the presence of about 0.6 mole of potassium carbonate at about 140° C. to prepare a phthalimide derivative, which corresponds to the formula

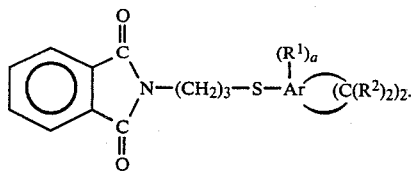

This product can thereafter be reacted with 1 mole of hydrazine hydrate at about 100° C. to prepare 3-aminopropylthio-substituted arylcyclobutene.

An alternative method for preparing a 2-aminoethylthioarylcyclobutene involves contacting a mercapto-substituted arylcyclobutene with 1 mole of ethyleneamine.

To prepare arylenethio-bridged N-arylcyclobutenyl cyclic imide, equimolar amounts of a mercaptoarylcyclobutene, sodium hydroxide and a halonitro-substituted aromatic compound are contacted in an alkanol solvent under reflux to prepare a nitroaryl arylcyclobutenyl sulfide. The nitro group on the nitroaryl arylcyclobutenyl sulfide is reduced by contacting one mole of such compound with about two moles of tin and about six moles of concentrated hydrochloric acid to prepare an aminoaryl arylcyclobutenyl sulfide. The aminoaryl arylcyclobutenyl sulfide is thereafter contacted with a cyclic anhydride in equimolar amounts in methylene chloride at a temperature of about 0° C. to about 25° C. to prepare an arylenethio-bridged N-arylcyclobutenyl amido alkenoic acid. The arylenethio-bridged N-arylcyclobutenyl amido alkenoic acid is dehydrated using procedures described hereinbefore to prepare an arylenethio-bridged N-arylcyclobutenyl cyclic imide.

The hydrocarbylenethio-bridged N-arylcyclobutenyl cyclic imides can be contacted with equimolar amounts of peracetic acid in an ethyl acetate solvent at between about 0° C. to 20° C. to prepare a hydrocarbylenesulfinyl-bridged N-arylcyclobutenyl cyclic imide. The hydrocarbylenethio-bridged N-arylcyclobutenyl cyclic imide can be contacted with about 2 moles of peracetic acid for each mole of the bridged cyclic imide in ethyl acetate solvent at about 0° C. to 20° C. to prepare a hydrocarbylenesulfonyl-bridged N-arylcyclobutenyl cyclic imide.

The hydrocarbyleneamido-bridged arylcyclobutenyl amido alkenoic acids can be prepared by the following procedures. In the first step, a compound substituted with both a nitro group and acid chloride moiety is reacted with an aminoarylcyclobutene in the presence of 1 equivalent of a trialkylamine, in a chlorinated hydrocarbon solvent at 0° C. and thereafter at 20° C. to prepare a nitrohydrocarbyleneamido-substituted arylcyclobutene. This reaction can be illustrated by the following equation

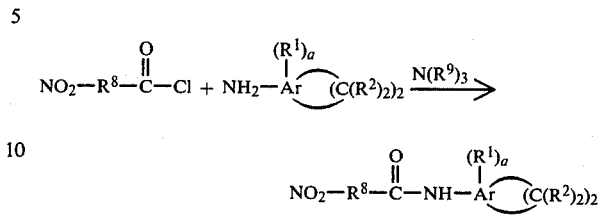

wherein $R^8$ is as previously defined, and $R^9$ is an alkyl group. The nitro group is thereafter reduced to an amino group by contacting the compound prepared in the previous reaction with hydrogen gas in excess in the presence of a palladium metal catalyst in an alkanol solvent at about 25° C. This product is an aminohydrocarbyleneamido-substituted arylcyclobutene which corresponds to the formula

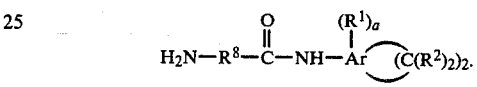

This aminohydrocarbyleneamido-substituted arylcyclobutene can thereafter be reacted with an unsaturated cyclic anhydride to prepare a hydrocarbyleneamido-bridged arylcyclobutenyl amido alkenoic acid, using the procedure described hereinbefore, as illustrated by the following equation

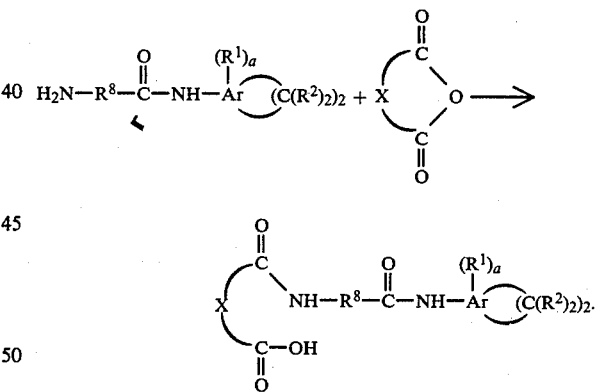

In one preferred embodiment, this process involves reacting a nitroaroyl chloride with the aminoarylcyclobutene to prepare a nitroarylamidoarylcyclobutene which can thereafter be hydrogenated to the aminoarylamidoarylcyclobutene, which is thereafter reacted with the unsaturated cyclic anhydride as described hereinbefore.

Alternatively, the alkyleneamido-bridged arylcyclobutenyl amido alkenoic acids can be prepared by the following process. In the first step, 1 mole of a cyclic lactone is reacted with an amino-substituted arylcyclobutene in toluene at about 100° C. to prepare a hydroxy alkyleneamido-substituted arylcyclobutene. This process is described by the following equation

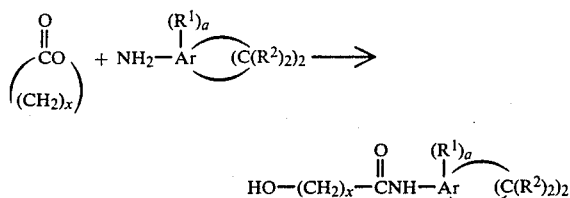

wherein x is 3 or greater. The hydroxyalkylamidearyl-cyclobutene is thereafter reacted with a 10 percent mole excess of thionyl chloride at about 70° C. to prepare a chloroalkylamide-substituted arylcyclobutene as described by the following equation

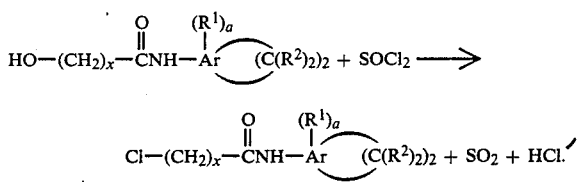

The chloroalkylamido-substituted arylcyclobutene is reacted with a 2 molar excess of sodium iodide in methanol at reflux to prepare a gamma-iodoalkylamidoaryl-cyclobutene. The gamma-iodoalkylamidoarylcyclobutene is thereafter reacted with a 10 percent mole excess of sodium nitrite in N,N-dimethylformamide solvent at 25° C. to prepare a gamma-nitroalkylamidoarylcyclobutene. The gamma-nitroalkylamidoarylcyclobutene is thereafter hydrogenated with excess hydrogen over a palladium metal catalyst in an ethanol solvent at about 20° C.–25° C. to prepare a gamma-aminoalkylamidoarylcyclobutene derivative. This gamma-aminoalkylamidoarylcyclobutene derivative can thereafter be reacted with an unsaturated cyclic anhydride under conditions described hereinbefore to prepare the alkyleneamido-bridged arylcyclobutenyl amido alkenoic acid. In preferred embodiments, the initial lactone is butyrolactone which prepares the propyleneamido-bridged species, a valerolactone starting material results in the preparation of the butyleneamido-bridged species, and the caprolactone starting material results in the pentyleneamido-bridged species.

The methyleneamido-bridged arylcyclobutenyl amido alkenoic acid can alternatively be prepared by the following sequence. Chloroacetyl chloride is reacted with an amino-substituted arylcyclobutene in the presence of a trialkylamine in methylene chloride at 0° C., then 20° C. to prepare an alpha-chloroacetamide-substituted arylcyclobutene. The alpha-chloroacetamidearylcyclobutene is thereafter reacted with a 2 molar excess of sodium iodide in methanol at reflux to prepare the iodoacetamidearylcyclobutene. The iodoacetamidearylcyclobutene can be converted to an aminoacetamide derivative, and thereafter to a methyleneamido-bridged arylcyclobutenyl amido alkenoic acid by the sequence of reactions described in the previous paragraph.

An alternative method for the preparation of an ethyleneamido-bridged arylcyclobutenyl amido alkenoic acid involves the following reaction sequence. One mole of acryloyl chloride is reacted with 1 mole of an amino-substituted arylcyclobutene in the presence of 1 mole of a trialkylamine, in a methylene chloride solvent at 0° C., then at 20° C. to prepare an acrylamide-substituted arylcyclobutene. Thereafter acrylamidearylcyclobutene is reacted with excess ammonia in ethanol at 20° C. to prepare a beta-aminopropionamidearylcyclobutene, which can thereafter be reacted with a cyclic unsaturated anhydride to prepare the ethyleneamido-bridged arylcyclobutenyl amido alkenoic acid.

An alkyleneoxy-bridged arylcyclobutenyl amido alkenoic acid can be prepared by the following sequence of reactions. A hydroxyarylcyclobutene is reacted with an alkyl group substituted with a bromo and chloro group in the presence of a molar equivalent of sodium hydroxide in ethanol at reflux to prepare a chloroalkyl ether of an arylcyclobutene. This reaction can be illustrated by the following reaction sequence wherein $R^{10}$ is an alkylene group.

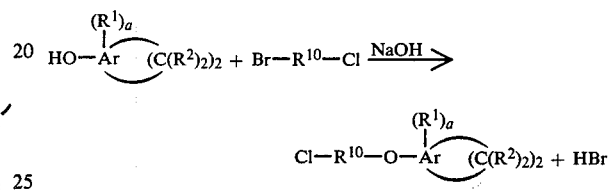

The chloroalkyl ether of the arylcyclobutene is thereafter reacted with a 2 molar excess of sodium iodide in methanol at reflux to prepare an iodoalkyl ether of the arylcyclobutene, which is thereafter reacted with sodium nitrite, a molar equivalent thereof, in N,N-dimethylformamide solvent at 25° C. to prepare a nitroalkyl ether of arylcyclobutene. The nitroalkyl ether of arylcyclobutene can be reduced with excess hydrogen over a palladium metal catalyst in an ethanol solvent at 25° C. to prepare an aminoalkyl ether of an arylcyclobutene. Such aminoalkyl ether of arylcyclobutene can thereafter be reacted with an unsaturated cyclic anhydride, under conditions described hereinbefore to prepare the alkyleneoxy-bridged arylcyclobutenyl amido alkenoic acids, as illustrated by the following equation

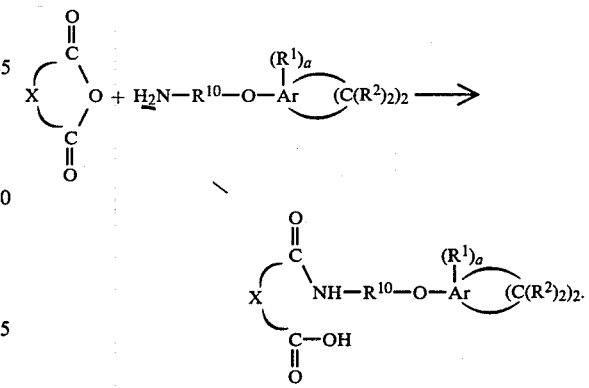

An aryleneoxy-, or alkaryleneoxy-bridged arylcyclobutenyl amido alkenoic acid can be prepared by the following sequence of reactions. An aromatic compound or alkyl-substituted aromatic compound substituted with a nitro group and a chloro group is reacted with a hydroxy-substituted arylcyclobutene in the presence of 2 equivalents of potassium carbonate in an N,N-dimethylformamide solvent to prepare a nitroaryl ether or nitroalkaryl ether of an arylcyclobutene. This reaction can be illustrated by the following equation. The nitroaryl ether, or nitroalkaryl ether of the arylcyclobutene can thereafter be contacted with two moles of ten and six moles of hydrochloric acid to reduce the nitro group to an amino group so as to prepare an aminoaryl ether or an aminoalkaryl ether of an arylcyclobutene. Alternatively, the nitro group may be reduced to an amino group by hydrogenation over a palladium metal catalyst in methanol or ethanol at about 25° C. and about 50 psi. Such compounds are thereafter reacted with cyclic unsaturated anhydrides as described hereinbefore to prepare the aryl ether-, or alkaryl ether-bridged arylcyclobutenyl amido alkenoic acids.

Hydrocarbylenecarbonyloxy-bridged arylcyclobutenyl amido alkenoic acids may be prepared by the following procedure. A hydrocarbon containing nitro and acid chloride moieties is reacted with 1 mole of a hydroxy-substituted arylcyclobutene in the presence of 1 mole of a trialkylamine in methylene chloride solvent at 0° C. and thereafter at 20° C. to prepare a nitrohydrocarbylenecarbonyloxy-substituted arylcyclobutene. This reaction is illustrated by the following equation

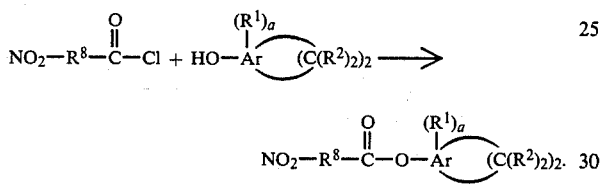

Thereafter the nitrohydrocarbylenecarbonyloxy-substituted arylcyclobutene is contacted with hydrogen gas in excess to hydrogenate the nitro group, and with 1 mole of hydrochloric acid in an ethanol solvent at about 25° C. to prepare an ammonium chloride salt-substituted hydrocarbylenecarbonyloxy-substituted arylcyclobutene as illustrated by the following ,quation

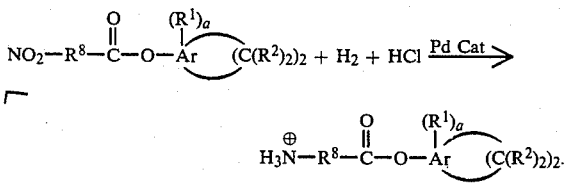

The ammonium chloride salt is thereafter reacted with an unsaturated cyclic anhyride in the presence of a trialkylamine as described hereinbefore to prepare a hydrocarbylenecarbonyloxy-bridged arylcyclobutenyl amido alkenoic acid.

Hydrocarbyleneoxycarbonyl-bridged arylcyclobutenyl amido alkenoic acids can be prepared by the following process. A hydrocarbon containing a hydroxy and nitro group is reacted with 1 mole of an acid chloride-substituted arylcyclobutene in the presence of a molar equivalent of a tri-alkylamine in methylene chloride solvent at 0° C., then at 20° C. to prepare a nitrohydrocarbyleneoxycarbonyl-substituted arylcyclobutene. This reaction is exemplified by the following equation

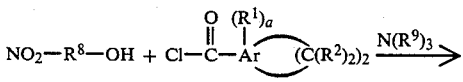

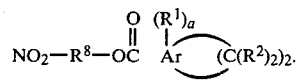

The nitrohydrocarbyleneoxycarbonyl-substituted arylcyclobutene is reacted with excess hydrogen and 1 mole of hydrochloric acid over a palladium catalyst in an ethanol solvent at about 25° C. to prepare an ammonium hydrochloride salt of a hydrocarbyleneoxycarbonylarylcyclobutene. This process is exemplified by the following equation

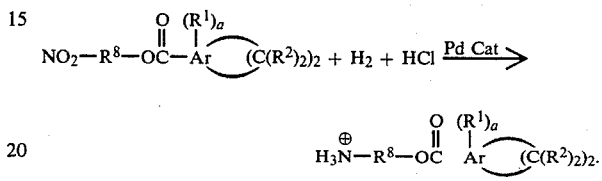

The ammonium hydrochloride salt can thereafter be reacted with an unsaturated cyclic anhydride as described hereinbefore to prepare a hydrocarbyleneoxycarbonyl-bridged arylcyclobutenyl amido alkenoic acid. This process is exemplified by the following equation

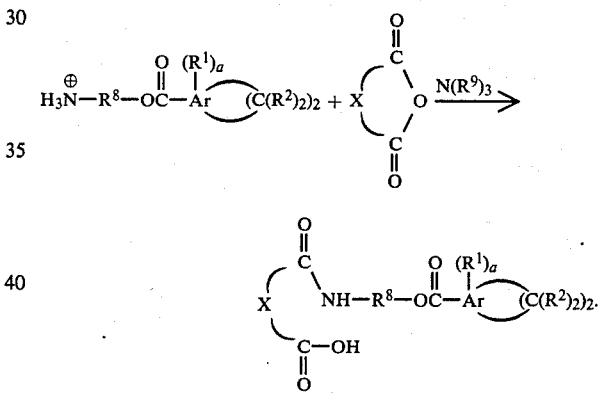

The compounds of this invention are unique in several respects. They have a latent intramolecular diene and dienophile functionality. They are thermally stable for long periods at elevated temperatures, up to 100° C. They are readily polymerizable. The compounds of this invention are useful in the preparation of polyimides by homopolymerization of the compounds of this invention. It is believed that the polymerization takes place by a Diels-Alder reaction wherein the unsaturation on the amido alkenoic acid acts a dienophile while the cyclobutene ring forms a diene which reacts with the dienophile to form the polymeric compositions. The compounds of this invention, when heated to polymerization temperature, lose a molecule of water and the amido alkenoic acid portion of the molecule cyclizes to an imido functionality.

The polymers of this invention are prepared by heating the compounds described hereinbefore to a temperature of 170° C. or greater. Preferable temperatures for polymerization are 200° C. or greater. In general, it is preferable to run the polymerization at a temperature of between about 170° C. and 300° C., with between about 200° C. and 300° C. being most preferred.

Wherein the arylcyclobutenyl amido alkenoic acid or a salt thereof corresponds to the formula

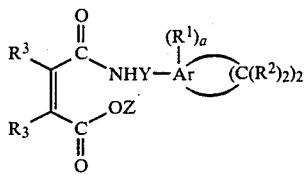

wherein Ar, $R^1$, $R^2$, $R^3$, X and a are as described hereinbefore; it is believed that the polymeric composition contains units which correspond to the formula

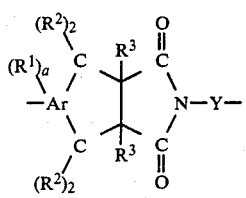

It is further believed that in one preferred embodiment the polymers derived from monomers of such a formula result in the preparation of polymers which correspond generally to the formula

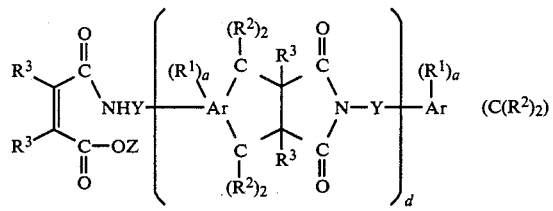

wherein Ar, $R^1$, $R^2$, $R^3$, Y, Z and a are as described hereinbefore and d is a real number of about 2 or greater, and most preferably 20 or greater.

In another preferred embodiment, the polymeric composition is the homopolymer of a compound which corresponds to the formula

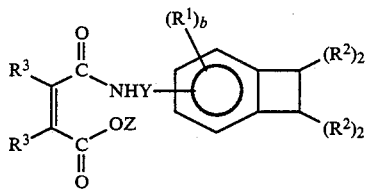

wherein $R^1$, $R^2$, $R^3$, Y, Z and b are as hereinbefore defined. In this embodiment, it is believed that the polymer prepared contains units which correspond to the formula

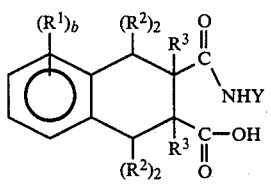

wherein $R^1$, $R^2$, $R^3$, Y, Z and b are as hereinbefore defined.

In one preferred embodiment wherein the compound polymerized corresponds to said formula, it is believed that the polymer prepared corresponds to the formula

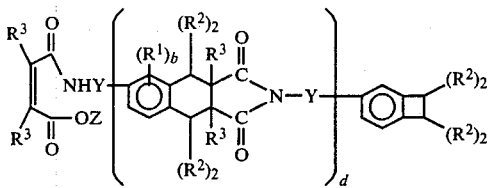

wherein $R^1$, $R^2$, $R^3$, Y, Z and b are as hereinbefore defined, and d is a real number of about 2 or greater. d is preferably about 20 or greater.

The novel arylcyclobutenyl amido alkenoic acids of this invention are useful in the preparation of polymeric compositions. In general, these polymeric compositions are prepared by contacting these arylcyclobutenyl amido alkenoic acids and heating them to the polymerization temperature of the particular monomer used. The polymerization is an addition polymerization. Furthermore, no catalyst initiator or curing agents are necessary for the polymerization to take place. It is believed that the polymerization takes place when the cyclobutene ring undergoes transformation to prepare an aryl radical with two olefinic unsaturated moieties ortho to one another wherein the olefinic unsaturated moieties thereafter undergo reaction with the unsaturation in the amido alkenoic acid. It is to be noted that the temperature at which polymerization is initiated is dependent upon the nature of substituents on the cyclobutene ring. In general, wherein the cyclobutene ring is unsubstituted, the polymerization is initiated at about 175° C. Wherein the cyclobutene ring is substituted with an electron-donating substituent, the polymerization temperature is generally lowered, the higher the ability of the substituent to donate electrons, the lower the polymerization initiation temperature is.

The novel compounds of this invention can be used to prepare coatings. The compounds are dissolved in an aqueous solution, which is thereafter coated onto a substrate. The water is evaporated from the substrate leaving a coating of the novel compounds. Thereafter, the coated substrate is exposed to temperatures at which the novel compounds of this invention undergo polymerization over a period of time for the polymerization to go to the desired degree of polymerization, resulting in a thermoset polymer coating on the substrate.

Under preferable conditions, temperatures of above 200° C. for between 1 and 5 hours are used. It is preferable to saturate the aqueous solution with the monomer, a 5 to 40 weight percent concentration of the monomer in the solvent is preferred.

The method of polymerization of the arylcyclobutenyl amido alkenoic acids has a significant effect on the nature and properties of the polymeric composition prepared. In one embodiment, the arylcyclobutenyl amido alkenoic acids of this invention can be melt polymerized. The melt polymerization of arylcyclobutenyl amido alkenoic acids allows their use in the preparation of solid parts, as coatings, in composites, as adhesives and as fibers.

In one embodiment of the melt polymerization, the monomer is heated to the temperature at which is melts, preferably this is a temperature of between about 80° C. and 100° C., and thereafter poured or injected into a mold. Thereafter, pressure is applied on the melted monomer in the mold. Generally, pressures of between about 100 and 2000 psi are suitable. Thereafter, the monomer is heated to a temperature at which the monomers undergo polymerization. This is preferably a temperature of between about 200° C. and 300° C., more preferably between about 200° C. and 250° C. for between about 10 minutes and 3 hours. Upon cooling, the polymerized composition can be removed from the mold.

Polymers prepared in this manner can subsequently be thermally treated at temperatures above 200° C. to raise the modulus and lower the coefficient of expansion of such polymeric compositions.

In general, the polymers prepared by this method are insoluble in that they swell but do not dissolve, are thermally stable at 200° C., have a good modulus, a low water pickup and are reasonably hard.

In another embodiment, the compounds of this invention can be used to prepare coatings and films. In such embodiments, the monomers are dissolved in a suitable solvent and coated onto the substrate of choice, and thereafter the coated substrate is exposed to temperatures at which the monomers undergo polymerization over a period of time sufficient for the polymerization to go to completion. Under preferable conditions, temperatures of above about 200° C. for between 1 and 5 hours are used. Suitable solvents are those which volatilize away at temperatures below the polymerization temperature. Preferred solvents are cyclic and aliphatic ethers, lower alkanols, amides, and chlorinated hydrocarbon solvents. It is preferable to saturate the solvent with the monomer, a 20 to 30 weight percent concentration of monomer in the solvent is preferred.

The arylcyclobutenyl amido alkenoic acids may be combined with the powder-form or fibrous fillers or reinforcing materials either before or after heat treatment. For example, it is possible to impregnate powder-form or fibrous fillers or reinforcing materials such as quartz sand or glass cloths, with the arylcyclobutenyl amido alkenoic acids, optionally in solution.

Suitable fillers and reinforcing materials are, generally, in any powder form and/or fibrous products, for example, of the type commonly used in the production of moldings based on unsaturated polyester resins or epoxide resins. Examples of products such as these are, primarily, granular fillers such as quartz powder, ground shale, asbestos powder, powdered corundum, chalk, iron powder, aluminum powder, sand, gravel and other fillers of this kind, also inorganic or organic fibers, more especially glass fibers in the usual textile forms of fibers, filaments rovings, yarns, nonwovens, mats and cloths, etc. In this connection, amino silane-based finishes have proven to be particularly effective. It is also possible to use corresponding textile structures of organic, preferably synthetic fibers (polyamides, polyesters) or on the basis of quartz, carbon, metals, etc., as well as monocrystals (whiskers).

The end products combined with fillers or reinforcing materials may be used in particular in vessel and pipe construction by the winding technique, in electrical engineering, in mold construction and tool making and also in the construction of heavily stressed components, in the lightweight construction of vehicles in aeronautical and astronautical engineering.

In another embodiment, the arylcyclobutenyl amido alkenoic acids can be used as adhesives. In such embodiment, one of the substrates to be joined is contacted with some form of the monomers, for example, the monomer in a powdered form. Thereafter, the second substrate to be adhesivated is contacted with the substrate previously contacted with the monomer. Thereafter, pressure of at least 1 psi is applied and the monomers and substrates are raised to a temperature at which the monomer undergoes polymerization.

In one embodiment, the arylcyclobutenyl amido alkenoic acids can be formed into a prepolymer which thereafter can be polymerized. To form the prepolymer, the arylcyclobutenyl amido alkenoic acids are contacted in an inert atmosphere or under vacuum and heated to a stage at which the polymerization mixture is sufficiently viscous enough to be moldable in conventional molding equipment. In general, the monomers can be contacted at a temperature of 190° C. to 220° C. for between about 1 and 10 minutes. Thereafter, the prepolymer can be used in various techniques to prepare the polymeric compositions of this invention. In one preferred embodiment, the prepolymer is cooled to form a powder which can be used to form compression molded articles, as an adhesive, and in many other uses. In another embodiment, a prepolymer of the arylcyclobutenyl amido alkenoic acids can be prepared by precipitation polymerization. In particular, the technique involves heating such monomers in a solvent to prepare a low molecular weight prepolymer that contains unreacted arylcyclobutene rings. A solvent is used which dissolves the monomer but not the prepolymer. As the prepolymer forms, it precipitates and is removed. The prepolymer can be fabricated in a hot compression mold which reacts out the remaining arylcyclobutene rings to give a thermoset polymer.

Preferable solvents are nonpolar solvents, such as aromatic hydrocarbons, aliphatic hydrocarbons, aliphatic chlorinated hydrocarbons, aromatic chlorinated hydrocarbon solvents, biphenols, naphthalenes or polychlorinated biphenols. The polymerization can take place at temperatures generally of between about 200° C. and 240° C. for periods of between about 1 and 5 hours. In general, the monomer can be dissolved up to saturation in the solvent used. A 20 to 30 percent by weight solution of the monomer in the solvent is preferred.

In another embodiment, the arylcyclobutenyl amido alkenoic acids can be polymerized by solution polymerization techniques. In this embodiment, the monomers are dissolved in dipolar aprotic solvents with boiling points above the polymerization temperature of the monomers. It is preferable that the solvents have a boiling point of above 200° C. and more preferable that the solvents have a boiling point of above 250° C. Examples of preferred dipolar aprotic solvents include amides and sulfones. It is necessary to add to the solution lithium salts which solubilize the monomer in the solvents, preferably between about 5 and 20 weight percent based on the monomer. A preferred lithium salt is lithium chloride. The polymerization takes place by heating the polymerization solution to a temperature at which the monomer undergoes polymerization, preferably above 200° C. The polymerization time is generally between about 1 and 10 hours. The polymer can be recovered by adding water to precipitate the polymer from the reaction solution and thereafter stripping off the solvent. The polymers prepared with this method can be used in compression moldings or to prepare coatings. It is often desirable to process these polymers under elevated temperatures.

In another embodiment, the monomers of this invention which undergo polymerization at a temperature which is below the melting point of the monomer can be polymerized in a solid state polymerization. In this method, the monomer is heated to a temperature at which polymerization takes place. Polymers prepared in this method can be useful in the preparation of bearings, seals and other parts by powder metallurgy techniques.

SPECIFIC EMBODIMENTS

The following examples are included to illustrate the invention, and do not limit the scope of the invention or the claims. Unless otherwise specified, all parts and percentages are by weight.

EXAMPLE 1

(a) Preparation of Ethyl 2-(o-Chlorobenzyl)Cyanoacetate

Into a 3-liter, three-necked flask equipped with a mechanical stirrer, reflux condenser, addition funnel and nitrogen inlet is placed a solution of 35.64 g (1.55 moles) of sodium metal in 1050 mm of absolute 2B ethanol. The solution is stirred under nitrogen and cooled to 0° C. in an ice bath and 763.56 g (6.75 moles) of ethyl cyanoacetate is added dropwise over a period of 15 minutes. To this white suspension is added 241.56 g (1.5 moles) to o-chlorobenzyl chloride dropwise over 1 hour. After the addition is complete, the ice bath is removed and the mixture is slowly heated under nitrogen to reflux and held there for 3 hours. The resulting pink-colored mixture is allowed to cool under nitrogen overnight at room temperature. About 1 liter of ethanol is distilled from the reaction mixture and 1.5 liters of water are added. The organic layer is taken up in three 400-ml portions of methylene chloride, and the solutions are combined and washed once with 150 ml of water. The methylene chloride solution is dried over anhydrous magnesium sulfate, filtered and evaporated on a rotary evaporator. The residual liquid is distilled under reduced pressure through an insulated 12-inch Vigreux column. A forerun of ethyl cyanoacetate (boiling point 55° C.–60° C./0.3 mm Hg) comes over first followed by pure ethyl 2-(o-chlorobenzyl)cyanoacetate. The infrared, 'H and $^{13}$C nuclear magnetic resonance are used to establish the structure. The yield is 68 percent of product having a boiling point of 130° C.–135° C./0.3 mm Hg.

(b) Preparation of 2-(o-Chlorobenzyl)Cyanoacetic Acid

In a 2-liter, three-necked flask equipped with a mechanical stirrer, addition funnel and nitrogen inlet is placed 243 g (1.02 moles) of ethyl 2-(o-chlorobenzyl)cyanoacetate. A solution of 54.52 g (1.363 moles) of sodium hydroxide pellets and 545 ml of water is added over a period of 15 minutes while stirring under nitrogen. Initially, the solution turns cloudy and then becomes clear. The resulting mixture is stirred for 5 hours at room temperature under nitrogen. Water (445 ml) is added and the mixture is cooled in an ice bath. Acidifying to pH 1 with 4N hydrochloric acid gives a fine white precipitate that is filtered and washed with water until neutral to litmus. The product is dried in a vacuum oven at 60° C. overnight to yield 20 g (97 percent) of white powder. This material is recrystallized from toluene to give pure white crystals of 2-(o-chlorobenzyl)cyanoacetic acid identified by infrared, 'H and $^{13}$C nuclear magnetic resonance. The yield is 94 percent of product having a melting point of 132° C.–134° C.

(c) Preparation of o-Chlorocinnamonitrile

Into a 1-liter, three-necked flask equipped with a mechanical stirrer, reflux condenser and nitrogen inlet is placed 138.5 g (0.66 mole) of 2-(o-chlorobenzyl)cyanoacetic acid and 220 ml of dry N,N-dimethylformamide. The mixture is stirred and slowly heated under nitrogen to reflux and held there for 6 hours. The resulting yellow mixture is allowed to cool under nitrogen overnight at room temperature. A precipitate (approximately 0.5 g) that forms is filtered off and the filtrate is poured into 1 liter of water. The organic layer is taken up in three 330-ml portions of ethyl ether/hexane (1:1 v/v), and the solutions are combined and washed once with 150 ml of water. The ethyl ether/hexane solution is dried over anhydrous magnesium sulfate, filtered and evaporated on a rotary evaporator. The residual liquid is distilled under reduced pressure through an insulated 12-inch Vigreux column with the product being collected at 82° C.–85° C./0.3 mm Hg as a colorless liquid identified by infrared, 'H and $^{13}$C nuclear magnetic resonance. The yield is 94.7 percent.

(d) Preparation of 1-Cyanobenzocyclobutene

A 3-liter, three-necked flask equipped with a dry ice condenser, mechanical stirrer and Claisen adapter fitted with an ammonia gas inlet and nitrogen inlet is rinsed with acetone, dried in an oven at 125° C., and heated with an air gun while flushing with nitrogen. The apparatus is cooled in a dry ice-acetone bath and the condenser is filled with a dry ice-acetone mixture. Ammonia gas flow is initiated and 600 ml is condensed out. The ammonia inlet tube is replaced by a stopper, and 0.4 g of powdered iron (III) nitrate is added. Sodium metal, 51.52 g (2.24 moles) is added in small portions over 1 hour. After all the sodium is added, the dry ice bath is removed and cooling is left to the dry ice condenser. Complete conversion of the sodium/ammonia solution to sodamide is indicated by a color change from deep blue to gray. Next, 92.82 g (0.56 mole) of o-chlorocinnamonitrile is added over a period of 10 minutes. The last traces of the nitrile are washed into the flask with small amounts of anhydrous ethyl ether. The dark green reaction mixture is stirred vigorously for 3 hours and then is treated with 134.4 g (1.68 moles) of solid ammonium nitrate. The ammonia is allowed to evaporate overnight at room temperature. Water (420 ml) is cautiously added to the residue. The organic layer is taken up in two 224-ml portions of chloroform, and the solutions are combined and washed twice with 140 ml of aqueous 5 percent hydrochloric acid and once with 140 ml of water. The chloroform solution is dried over anhydrous magnesium sulfate, filtered, and evaporated on a rotary evaporator. The residual liquid is distilled under reduced pressure through an insulated 12-inch Vigreux column. The product is collected at 59° C.–69° C./0.2 mm Hg. The infrared, 'H and $^{13}$C nuclear magnetic resonance are run to identify the product. The yield is 50 percent.

(e) Preparation of 5-nitro-1-cyanobenzocyclobutene

Into a 500-ml, three-necked flask equipped with an addition funnel, thermometer and nitrogen inlet is placed 14.1 g (0.17 mole) of sodium nitrate and 135 ml of concentrated sulfuric acid. The mixture is stirred under nitrogen while cooling to −5° C. (calcium chloride/ice) and 19.5 g (0.16 mole) of 1-cyanobenzocyclobutene is added dropwise at such a rate as to keep the reaction temperature below 2° C. The reaction mixture is then stirred under nitrogen at 0° C.-5° C. for 0.5 hour, poured onto 1050 g of ice, and extracted with four 300-ml portions of methylene chloride. The methylene chloride solutions are combined, washed with four 150-ml portions of 10 percent sodium bicarbonate, once with 300 ml of water, and dried over anhydrous magnesium sulfate. The methylene chloride solution is filtered and evaporated on a rotary evaporator to give 26.9 g of residue which is recrystallized from absolute 2B ethanol to give pure 5-nitro-1-cyanobenzocyclobutene identified by infrared, 'H and $^{13}$C nuclear magnetic resonance. The melting point is 110° C.-112° C. and the yield is 64.1 percent.

(f) Preparation of 5-Amino-1-Cyanobenzocyclobutene

Into a 1-liter, three-necked flask equipped with a gas dispersion tube, reflux condenser, rubber septum and nitrogen inlet is placed 7 g (0.04 mole) of 5-nitro-1-cyanobenzocyclobutene and 400 ml of absolute 2B ethanol. The mixture is stirred under nitrogen and heat is applied to dissolve the solid. After adding 2.4 ml of glacial acetic acid and 1.6 g of 5 percent palladium on carbon, hydrogen flow is initiated and the mixture is hydrogenated at atmospheric pressure and ambient temperature. The hydrogenation is followed by thin-layer chromatography (silica gel; 70 percent toluene, 25 percent ethyl acetate, 5 percent triethylamine as eluent) and this shows the reaction is essentially complete in 1 hour. After 3 hours, the hydrogen flow is stopped and the system is purged with nitrogen for 15 minutes to remove excess hydrogen gas. The catalyst is removed by filtration using Celite and quickly quenched in water. The filtrate is evaporated to dryness on a rotary evaporator and the residue is treated with aqueous 10 percent sodium hydroxide. The aqueous solution is extracted with three 100-ml portions of ethyl ether, and the solutions are combined and washed once with 100 ml of water. The ethyl ether solution is dried over anhydrous potassium carbonate, filtered and evaporated on a rotary evaporator to give an amber-colored oil that solidified on standing. The product is pumped under vacuum overnight to remove the last traces of ethyl ether and stored under nitrogen. The infrared, 'H and $^{13}$C nuclear magnetic resonance are run. The yield is 86.4 percent.

(g) Preparation of N-[5-(1-Cyanobenzocyclobutenyl)]maleamic Acid

Into a 250-ml, three-necked flask equipped with a mechanical stirrer, addition funnel, reflux condenser, thermometer and nitrogen inlet is placed 4.9 g (0.05 mole) of freshly sublimed maleic anhydride and 50 ml of dry chloroform. The mixture is stirred under nitrogen while cooling to 15° C. in an ice bath and a solution of 7 g (0.05 mole) of 5-amino-1-cyanobenzocyclobutene in 50 ml of dry chloroform is added dropwise at such a rate as to keep the reaction mixture below 20° C. The reaction is maintained below 20° C. and stirred under nitrogen for 1 hour after addition is complete. The solid N-[5-(1-cyanobenzocyclobutenyl)]maleamic acid is filtered off, washed with cold chloroform, then with hot ethyl acetate/2B ethanol (absolute; 1:1 v/v), and dried overnight in a vacuum oven at 60° C. The infrared, 'H and $^{13}$C nuclear magnetic resonance, and carbon, hydrogen, nitrogen analyses are run.

| Analysis | Calculated | Found |
|---|---|---|
| carbon | 64.46 | 63.80 |
| hydrogen | 4.16 | 4.44 |
| nitrogen | 11.57 | 11.36 |

The yield is 11.32 g equal to 94.25 percent and the melting point is 190° C.-192° C.

EXAMPLE 2

Preparation of N-[5-(1-Cyanobenzocyclobutenyl)]maleimide

Into a 250-ml, three-necked flask equipped with a mechanical stirrer, reflux condenser, thermometer and nitrogen inlet is placed 11 g (0.045 mole) of N-[5-(1-cyanobenzocyclobutenyl)]maleamic acid, 2.4 g (0.03 mole) of anhydrous sodium acetate, and 45.94 g (0.765 mole) of fresh glacial acetic acid. The mixture is stirred and slowly heated under nitrogen until a clear yellow solution results (117° C.-118° C.). After 5 minutes the heat is removed and the reaction mixture is allowed to cool under nitrogen overnight at room temperature. It is then slowly poured into a vigorously stirred slurry of ice and water (120 g total), and the resulting yellow precipitate filtered, washed with water until neutral to litmus, and transferred to a 500-ml beaker containing 150 ml of aqueous saturated sodium bicarbonate. This mixture is stirred for 10 minutes, then 150 ml of chloroform is added and stirred for an additional 10 minutes. The organic layer is taken up in three 50-ml portions of chloroform, and the solutions are combined and washed once with 150 ml of water. The chloroform solution is dried over anhydrous magnesium sulfate, filtered and evaporated on a rotary evaporator to give a viscous yellow oil. The product is pumped under vacuum overnight to give a yellow solid that is purified by column chromatography on silica gel using 70 percent toluene/30 percent ethyl acetate as the eluent. The infrared, 'H and $^{13}$C nuclear magnetic resonance, and carbon, hydrogen, nitrogen analyses are run.

| Analysis | Calculated | Found |
|---|---|---|
| carbon | 69.60 | 69.30 |
| hydrogen | 3.60 | 3.70 |
| nitrogen | 12.50 | 12.34 |

The yield is 5.7 g equal to 56.5 percent. The melting point is 55° C.-60° C.

EXAMPLE 3

Polymerization of N-[5-(1-Cyanobenzocyclobutenyl)]maleamic acid

In a 25-ml one-neck flask equipped with a nitrogen purge tube is placed 0.1127 g of N-[5-(1-cyanobenzocyclobutenyl)]maleamic acid and 10 drops of water. To this is added 4 drops of concentrated (15M) ammonia water. All of the solids dissolve. Nitrogen is bubbled through the solution until all the excess ammonia is gone. The solution is then coated onto microscope slides, and the water is allowed to evaporate at room temperature. The slides are then heated in air at 175° C. for 20 minutes to form a polymer coating. The coating

What is claimed is:

1. A compound which comprises an amido alkenoic acid or water-soluble salt thereof and an arylcyclobutene moiety, wherein the cyclobutene moiety is fused to the aryl radical, and wherein the amide nitrogen is connected to the aryl radical of the arylcyclobutene moiety by a bridging member or a direct bond.

2. The compound of claim 1 wherein the aryl radical is bound to the amido alkenoic acid by a direct bond or a bridging member which comprises a divalent organic radical.

3. The compound of claim 2 wherein the amido alkenoic acid can be substituted with a hydrocarbyl, hydrocarbyloxy or hydrocarbylthio group; the aryl radical can be substituted with a hydrocarbyl, electron-donating or electron-withdrawing group; and the cyclobutene ring can be substituted with an electron-withdrawing group.

4. The compound of claim 3 wherein the divalent organic radical is a hydrocarbylene, hydrocarbyleneamido, hydrocarbylenecarbonyloxy, hydrocarbyleneoxy, hydrocarbylenethio, hydrocarbylenesulfinyl or hydrocarbylenesulfonyl.

5. The compound of claim 4 wherein the hydrocarbylene moiety is alkylene, arylene, alkylene-bridged polyarylene, alkenylene-bridged polyarylene or cycloalkylene-bridged polyarylene.

6. The compound of claim 5 wherein the aryl moiety and the amido alkenoic acid are connected by a direct bond or a bridging member which comprises an alkylene, arylene, alkylene-bridged polyarylene, alkenylene-bridged polyarylene or cycloalkylene-bridged polyarylene.

7. The compound of claim 6 wherein the aryl moiety and the amido alkenoic acid are connected by a direct bond or a bridging member which comprises an alkylene or arylene moiety.

8. The compound of claim 7 wherein the aryl radical is a benzene radical.

9. The compound of claim 8 wherein the aryl moiety and the amido alkenoic acid are connected by a direct bond.

10. A compound which corresponds to the formula

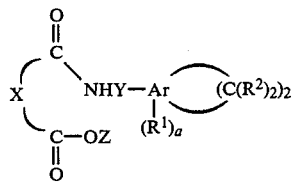

wherein
Ar is an aromatic radical;
$R^1$ is separately in each occurrence a hydrocarbyl, hydrocarbyloxy, hydrocarbylthio, electron-donating or electron-withdrawing group;
$R^2$ is separately in each occurrence hydrogen or an electron-withdrawing group;
X is an alkenylene moiety which can be substituted with one or more hydrocarbyl, hydrocarbyloxy or hydrocarbylthio groups;
Y is a direct bond or divalent organic moiety;
Z is hydrogen or a cation derived from ammonia, a primary or secondary amine, an alkali metal base or alkaline earth metal base; and
a is an integer of between about 0 and 3.

11. The compound of claim 10 which corresponds to the formula

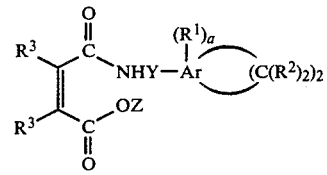

wherein
Ar is an aromatic radical;
$R^1$ separately in each occurrence a hydrocarbyl, hydrocarbyloxy, hydrocarbylthio, an electron-donating or electron-withdrawing group;
$R^2$ is separately in each occurrence hydrogen or an electron-withdrawing group;
$R^3$ is separately in each occurrence hydrogen, a hydrocarbyl, hydrocarbyloxy or hydrocarbylthio group;
Y is a direct bond or a divalent organic radical;
Z is hydrogen or a cation derived from ammonia, a primary or secondary amine, an alkali metal base or alkaline earth metal base; and
a is an integer of between about 0 and 3.

12. The compound of claim 11 which corresponds to the formula

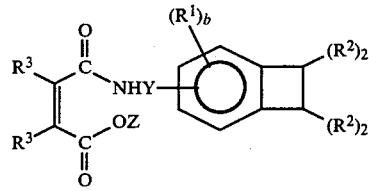

wherein
$R^1$ is separately in each occurrence a hydrocarbyl, hydrocarbylthio, hydrocarbyloxy, electron-withdrawing or electron-donating group;
$R^2$ is separately in each occurrence hydrogen or an electron-withdrawing group;
$R^3$ is separately in each occurrence hydrogen, hydrocarbyl, hydrocarbyloxy or hydrocarbylthio;
Y is a direct bond or a divalent organic radical;
Z is hydrogen or a cation derived from ammonia, a primary or secondary amine, an alkali metal base or alkaline earth metal base; and
b is an integer of between 0 and 3, inclusive.

13. The compound of claim 12 wherein
$R^1$ is $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ alkaryl, $C_{7-20}$ alkaryloxy, $C_{7-20}$ alkarylthio, $C_{7-20}$ aralkyl, $C_{7-20}$ aralkoxy, $C_{7-20}$ aralkylthio, cyano, carboxylate, hydrocarbylcarbonyloxy, nitro, halo, hydrocarbylsulfinyl, hydrocarbylsulfonyl or amino;
$R^2$ is hydrogen, cyano, carboxylate, hydrocarbylcarbonyloxy, nitro, halo, hydrocarbylsulfonyl or hydrocarbylsulfinyl;
$R^3$ is hydrogen, $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ alkaryl, $C_{7-20}$ alkaryloxy, $C_{7-20}$ alkarylthio, $C_{7-20}$ aralkyl, $C_{7-20}$ aralkoxy or $C_{7-20}$ aralkylthio; and
b is 0 or 1.

14. The compound of claim 13 wherein $R^1$ is $C_{1-20}$ alkyl, halo, nitro or cyano; $R^2$ is hydrogen, halo, nitro or cyano; and $R^3$ is hydrogen or $C_{1-20}$ alkyl.

15. The compound of claim 14 wherein $R^1$ is $C_{1-3}$ alkyl, halo, nitro or cyano; $R^2$ is hydrogen or cyano; and $R^3$ is hydrogen or $C_{1-3}$ alkyl.

16. The compound of claim 15 wherein $R^2$ is hydrogen; $R^3$ is hydrogen; and b is 0.

17. The compound of claim 16 wherein Y is a direct bond, a hydrocarbylene, hydrocarbyleneamido, hydrocarbylenecarbonyloxy, hydrocarbyleneoxy, hydrocarbyleneamino, hydrocarbylenecarbonyl, hydrocarbylenethio, hydrocarbylenesulfinyl or hydrocarbylenesulfonyl.

18. The compound of claim 17 wherein Y is a direct bond, alkylene, arylene, alkylene-bridged polyarylene, cycloalkylene-bridged polyarylene, alkenylene-bridged polyarylene, alkyleneamido, aryleneamido, alkylenecarbonyloxy, arylenecarbonyloxy, arylenecarbonyl, alkylenecarbonyl, aryleneoxy, alkyleneoxy, aryleneamino, alkyleneamino, alkylenethio, alkylenepolythio, arylenethio, arylenepolythio, arylenesulfinyl, alkylenesulfinyl, arylenesulfonyl, arylenesulfinyl, alkylenesulfinyl, arylenesulfonyl or alkylenesulfonyl.

19. The compound of claim 18 wherein Y is alkylene or arylene.

* * * * *

UNITED STATES PATENT AND TRADEMARK OFFICE
CERTIFICATE OF CORRECTION

PATENT NO. : 4,638,078

DATED : January 20, 1987

INVENTOR(S) : Robert A. Kirchhoff

Page 1 of 8

It is certified that error appears in the above-identified patent and that said Letters Patent is hereby corrected as shown below:

Face of Letters Patent under OTHER PUBLICATIONS reference to Fortschr., etc. "(19061)" should read -- (1961) --.

Col. 1, line 43 "aromtic" should read -- aromatic --.

Col. 4, between lines 55 and 60 the structure

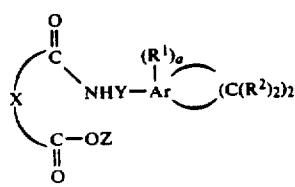

should be as follows:

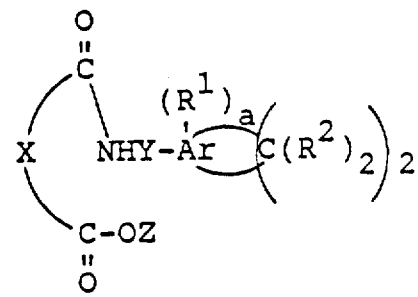

Col. 6, line 37, "$(R^6)_a N^{\oplus}(H)_b$" should be
-- $(R^6)_a{-}N^{\bullet}{-}(H)_b$ --.

UNITED STATES PATENT AND TRADEMARK OFFICE
CERTIFICATE OF CORRECTION

PATENT NO. : 4,638,078
DATED : January 20, 1987
INVENTOR(S) : Robert A. Kirchhoff It is certified that error appears in the above-identified patent and that said Letters Patent is hereby corrected as shown below:

Col. 8, between lines 30 and 35, the formula

should be

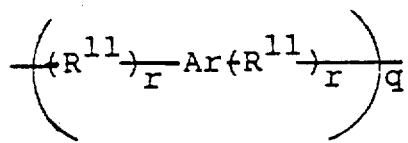

Col. 11. between lines 60 and 65, the formula

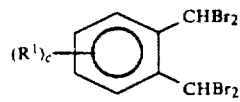

should be

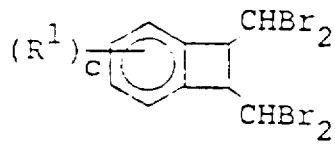

UNITED STATES PATENT AND TRADEMARK OFFICE
CERTIFICATE OF CORRECTION

PATENT NO. : 4,638,078

DATED : January 20, 1987

INVENTOR(S) : Robert A. Kirchhoff

Page 3 of 8

It is certified that error appears in the above-identified patent and that said Letters Patent is hereby corrected as shown below:

Col. 14, line 39, "alkylene" should read -- alkenylene --.

Col. 17, between lines 10 and 15, the formula

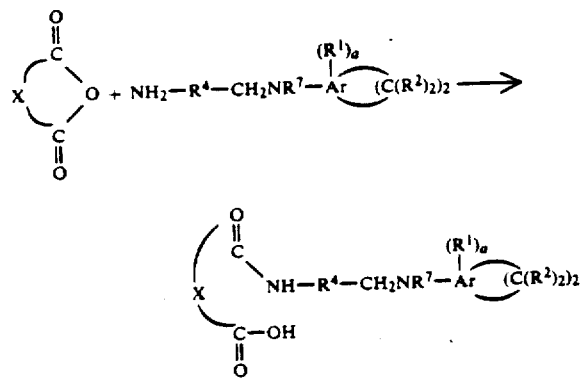

should be (next page)

UNITED STATES PATENT AND TRADEMARK OFFICE
CERTIFICATE OF CORRECTION

PATENT NO. : 4,638,078
DATED : January 20, 1987
INVENTOR(S) : Robert A. Kirchhoff It is certified that error appears in the above-identified patent and that said Letters Patent is hereby corrected as shown below:

continuance of previous correction:

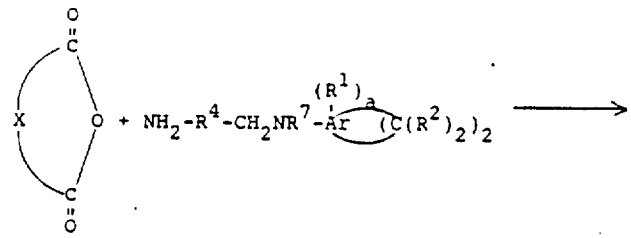

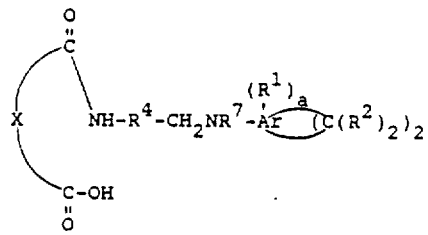

Col. 17, the equation between lines 30 and 35

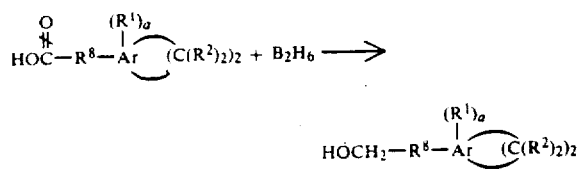

UNITED STATES PATENT AND TRADEMARK OFFICE
CERTIFICATE OF CORRECTION

PATENT NO. : 4,638,078
DATED : January 20, 1987
INVENTOR(S) : Robert A. Kirchhoff It is certified that error appears in the above-identified patent and that said Letters Patent is hereby corrected as shown below:

(continuance of previous correction) equation should be

Col. 18, line 20, the formula

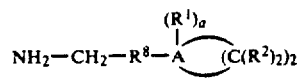

should be

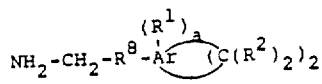

UNITED STATES PATENT AND TRADEMARK OFFICE
CERTIFICATE OF CORRECTION

PATENT NO. : 4,638,078
DATED : January 20, 1987
INVENTOR(S) : Robert A. Kirchhoff It is certified that error appears in the above-identified patent and that said Letters Patent is hereby corrected as shown below:

Col. 18, the formula between lines 30 and 45

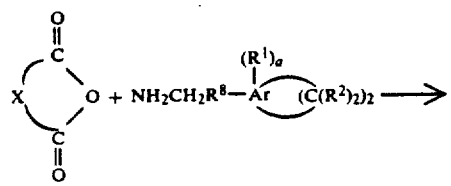

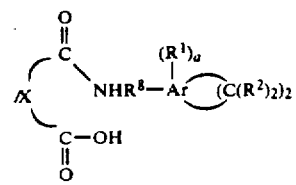

should be

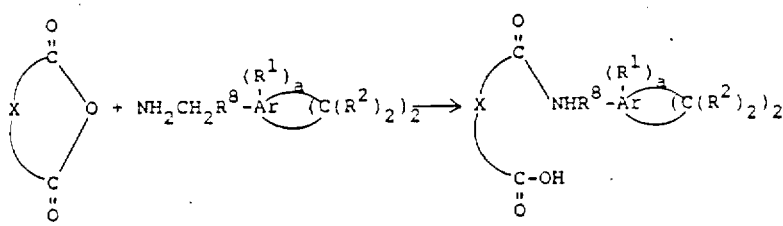

UNITED STATES PATENT AND TRADEMARK OFFICE
CERTIFICATE OF CORRECTION

PATENT NO.  : 4,638,078

DATED       : January 20, 1987

INVENTOR(S) : Robert A. Kirchhoff

It is certified that error appears in the above-identified patent and that said Letters Patent is hereby corrected as shown below:

Col. 27, the formula between lines 30 and 40

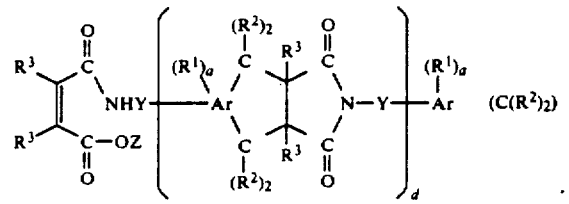

should be

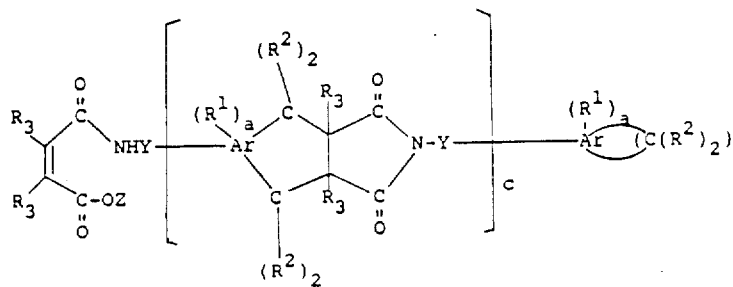

UNITED STATES PATENT AND TRADEMARK OFFICE
CERTIFICATE OF CORRECTION

PATENT NO. : 4,638,078
DATED : January 20, 1987
INVENTOR(S) : Robert A. Kirchhoff It is certified that error appears in the above-identified patent and that said Letters Patent is hereby corrected as shown below:

Col. 36, line 18, "$R^1$ separately, etc." should read -- $R^1$ is separately --.

Col. 38, lines 10 and 11, after the word "arylenepolythio", please delete "arylenesulfinyl, alkylenesulfinyl, arylensulfonyl".

Signed and Sealed this

Twenty-second Day of December, 1987

Attest:

DONALD J. QUIGG

*Attesting Officer*     *Commissioner of Patents and Trademarks*